(12) United States Patent
Nishida et al.

(10) Patent No.: US 8,993,598 B2
(45) Date of Patent: Mar. 31, 2015

(54) PYRROLE COMPOUNDS

(71) Applicant: Takeda Pharmaceutical Company Limited, Osaka-shi (JP)

(72) Inventors: Haruyuki Nishida, Kanagawa (JP); Yasuyoshi Arikawa, Kanagawa (JP); Ikuo Fujimori, Kanagawa (JP)

(73) Assignee: Takeda Pharmaceutical Company Limited, Osaka-shi (JP)

( * ) Notice: Subject to any disclaimer, the term of this patent is extended or adjusted under 35 U.S.C. 154(b) by 0 days.

(21) Appl. No.: 14/043,018

(22) Filed: Oct. 1, 2013

(65) Prior Publication Data

US 2014/0031393 A1    Jan. 30, 2014

Related U.S. Application Data

(62) Division of application No. 13/061,078, filed as application No. PCT/JP2009/065279 on Aug. 26, 2009, now Pat. No. 8,592,597.

(30) Foreign Application Priority Data

Aug. 27, 2008   (JP) .................................. 2008/218851
Oct. 17, 2008   (JP) .................................. 2008/269099

(51) Int. Cl.
    *A61K 31/4439*    (2006.01)
    *A61K 31/444*    (2006.01)
    *C07D 401/14*    (2006.01)

(52) U.S. Cl.
    CPC ............ *A61K 31/444* (2013.01); *C07D 401/14* (2013.01)
    USPC ....................................................... 514/333

(58) Field of Classification Search
    USPC ....................................................... 514/333
    See application file for complete search history.

(56) References Cited

U.S. PATENT DOCUMENTS

| | | | |
|---|---|---|---|
| 5,286,742 A | 2/1994 | Henegar et al. | |
| 5,331,006 A | 7/1994 | Horwell et al. | |
| 5,480,902 A | 1/1996 | Addor et al. | |
| 6,365,620 B2 | 4/2002 | Eberie et al. | |
| 6,727,270 B2 | 4/2004 | Kelly et al. | |
| 6,919,359 B2 | 7/2005 | Piotrowski et al. | |
| 7,186,716 B2 | 3/2007 | Wei et al. | |
| 2002/0193410 A1 | 12/2002 | Burns et al. | |
| 2007/0060623 A1 | 3/2007 | Kajino et al. | |
| 2008/0038368 A1 | 2/2008 | Geibel et al. | |
| 2008/0139639 A1 | 6/2008 | Kajino et al. | |
| 2009/0118335 A1 | 5/2009 | Hasuoka et al. | |
| 2009/0318429 A1 | 12/2009 | Doyle et al. | |
| 2010/0056577 A1 | 3/2010 | Nishida et al. | |

FOREIGN PATENT DOCUMENTS

| | | |
|---|---|---|
| EP | 0 259 085 A1 | 3/1988 |
| EP | 0464845 A1 | 1/1992 |

(Continued)

OTHER PUBLICATIONS

Cecil Textbook of Medicine, Bennett et al. ed W.B. Saunders Co., Philadelphie, 1997, 20$^{th}$ ed, vol. 1, 1004-1010.*

(Continued)

*Primary Examiner* — Patricia L Morris
(74) *Attorney, Agent, or Firm* — Mintz Levin Cohn Ferris Glovsky and Popeo, P.C.; David G. Conlin

(57) ABSTRACT

The present invention relates to a compound represented by the formula:

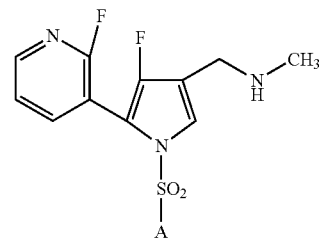

wherein A is pyridyl group having at least one substituent

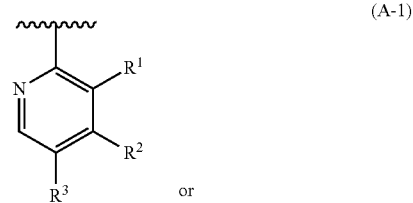

(A-1)

or

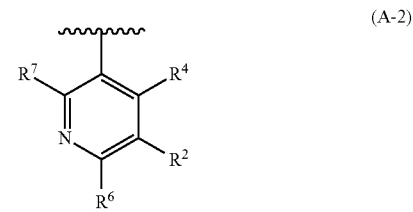

(A-2)

wherein $R^1$, $R^2$ and $R^3$ are each a hydrogen atom, a halogen atom, a $C_{1-6}$ alkyl group optionally substituted by halogen or a $C_{1-6}$ alkoxy group optionally substituted by halogen, $R^4$ and $R^6$ are each a hydrogen atom, a halogen atom or a $C_{1-6}$ alkyl group optionally substituted by halogen, $R^5$ is a hydrogen atom, a halogen atom, a $C_{1-6}$ alkyl group optionally substituted by halogen or a $C_{1-6}$ alkoxy group optionally substituted by halogen, and $R^7$ is a hydrogen atom or a $C_{1-6}$ alkyl group optionally substituted by halogen or a salt thereof, or a pharmaceutical composition containing the same.

3 Claims, 3 Drawing Sheets

(56) References Cited

FOREIGN PATENT DOCUMENTS

| | | |
|---|---|---|
| EP | 0538231 | 4/1993 |
| EP | 0597291 A1 | 5/1994 |
| EP | 1061075 A2 | 12/2000 |
| EP | 1176139 | 1/2002 |
| EP | 1284260 A1 | 2/2003 |
| EP | 1432693 A2 | 6/2004 |
| EP | 1466902 A1 | 10/2004 |
| EP | 1477489 A1 | 11/2004 |
| EP | 1655284 | 5/2006 |
| EP | 1803709 A1 | 7/2007 |
| JP | 63-63678 | 3/1988 |
| JP | 08-119936 | 5/1996 |
| JP | 9-30967 A | 2/1997 |
| JP | 11-209344 | 8/1999 |
| JP | 2004-315511 | 11/2004 |
| WO | WO-92/04025 | 3/1992 |
| WO | WO-93/09100 | 5/1993 |
| WO | WO-98/08815 A1 | 3/1998 |
| WO | WO-98/28269 | 7/1998 |
| WO | WO-00/58285 | 10/2000 |
| WO | WO-02/02524 | 1/2002 |
| WO | WO-02/02554 | 1/2002 |
| WO | WO-03/028641 A2 | 4/2003 |
| WO | WO-03/040147 | 5/2003 |
| WO | WO-03/044011 | 5/2003 |
| WO | WO-03/068738 | 8/2003 |
| WO | WO-03/068740 | 8/2003 |
| WO | WO-03/070729 | 8/2003 |
| WO | WO-03/106427 | 12/2003 |
| WO | WO-2004/014368 | 2/2004 |
| WO | WO-2004/103968 | 12/2004 |
| WO | WO-2006036024 A1 | 4/2006 |
| WO | WO-2007/026916 A1 | 3/2007 |
| WO | WO-2007/114338 A1 | 10/2007 |
| WO | WO-2008/108380 | 9/2008 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Golub et al, Science, vol. 286, Oct. 15, 1999, pp. 531-537.*
Lamers, "Is there s Need, etc.," Digestion 1989; 44 (suppl 1):4-8.*
Zollinger-Ellison syndrome—Mayo Clinic.com—print May 16, 2012.*
Weber et al., "Studies on the, etc.," Gastroenterology 1997;112: 84-91.*
Monkemuller et al., "Drug treatment, etc.," World J Gastroenterol 2006: 12(17) 2694-2700.*
Talley et al., "Efficacy of omeprazole, etc.," Aliment Pharmacol Ther 1998; 12: 1055-1065.*
Kuipers, "*Helicobacter pylori*, etc.," Aliment Pharmacol Ther 1997: 11 (Suppl. 1), 71-88.*
Schubert, "Gastric Secretion", Current Opinion in Gastroenterology 2007, 23:595-601.*
Sherman et al., "Role of Sonic, etc.," World J Gastrointest Pathophysiol Dec. 15, 2011; 2(6): 103-108.*
Kuipers et al., "Review Article, etc.," Aliment Pharmacol Ther 1995, 9: 331-340.*
Kandulski et al. II, "*Helicobacter pylori*, etc.," Curr Opin Gastroenterol 2014, 30:402-407.*
Freston, "Review Article, etc.," Aliment Pharmacol Ther 2001:15 (Suppl 2), 2-5.*
Venerito et al., "Interaction of, etc.," *Helicobacter* 15: 239-250 (2010).*
Artico, et al, "Structure-Based Design, Synthesis, and Biological Evaluation of Novel Pyrrolyl Aryl Sulfones: HIV-1 Non-Nucleoside Reverse Transcriptase Inhibitors Active at Nanomolar Concentrations," J. Med. Chem., XP002544396, 43:1886-1891 (2000).

Banker et al, Modern Pharmaceutics, 3rd ed., Marcel Dekker, New York, 1996, pages 451 and 596.
International Search Report for corresponding International Application No. PCT/JP2008/053890 (6 pages), issued Apr. 16, 2009.
International Search Report for corresponding International Application No. PCT/JP2009/065279 (3 pages). Issued Mar. 4, 2010.
Database Beilstein, Beilstein Institute for Organic Chemistry, Frankfurt-Main, XP002544400 dated Sep. 3, 2009.
Database Beilstein: Beilstein Institute for Organic Chemistry, Frankfurt-Main, DE; XP002544398; Database Accession No. 4491404 (BRN); Database Accession Nos. 4511053, 4534506, 4549375, 4558933, 4573102, 4575926, 4577349, 4582906, 4592993, 4594785, 4600861, 4602984, 4605482, 4607805, 4612106, 4615190 (BRNs). *abstract*. dated Sep. 3, 2009.
Database Beilstein: Beilstein Institute for Organic Chemistry, Frankfurt-Main, DE; XP002544401; Database Accession No. 6443954 (BRN); Database Accession Nos. 6448183, 6448193, 6448674, 6449474, 6450364, 6453034, 6453229, 6453629, 6455895, 6457232 (BRNs). *abstract* dated Sep. 3, 2009.
Database Beilstein: Beilstein Institute for Organic Chemistry, Frankfurt-Main, DE; XP002544399; Database Accession No. 4511416 (BRN); Database Accession Nos. 4517986, 4539949, 453117, 4572075, 4574392, 4582793, 4586769, 4600919, 4606368, 4610346, 4612195 (BRNs). *abstract* dated Sep. 3, 2009.
Database Beilstein; Beilstein Institute for Organic Chemistry, Frankfurt-Main, DE; XP002544397; Database Accession No. 4558323 (BRN); Database Accession Nos. 4559246, 4574723, 4581745, 4584939, 4586270, 4588621, 4595969, 4595971, 4596723, 4600812, 4600844, 4604026 (BRNs). *abstract* dated Sep. 3, 2009.
European Search Report for corresponding European Application No. EP 05 79 0387 completed on Sep. 17, 2009.
http://en.wikipedia.org/wiki/Gastric_cancer [online], [retrieved on Dec. 28, 2006]. Retrieved from the Internet, URL; http://en.wikipedia.org/wiki/Sjogren's_syndrome.
Ichikawa, et al, "5-endo Heck-type cyclization of 2-(trifluoromethyl)allyl ketone oximes: synthesis of 4-difluoromethylene-substituted 1-pyrrolines", Chemical Communication, Nov. 13, 2006, No. 42, pp. 4425-4427, XP 002513503, ISSN: 1359-7345.
Medical Encyclopedia: Zollinger-Ellison syndrome [online], [retrieved on Aug. 27, 2007]. Retrieved from the Internet, URL; http://www.nlm.nih.gov/medlineplus/print/ency/article/000325.htm.
Merck Manual Online, "Stomach Cancer": Section: Gastrointestinal Disorders, Subject: Tumors of the GI Tract. Last revisions: Dec. 2007, pp. 1 to 3. Retrieved on Oct. 8, 2008 from: http://www.merck.com/mmpe/sec02/ch021/ch021d.html?qt=gastric_cancer&alt=sh.
Obach: "Drug-Drug Interactions: An Important Negative Attribute in Drugs", Drugs of Today, 2003, 39(5): 301-338.
Okabe et al, "The Second Generation Synthesis of a Tumor Promoter Pendolmycin," *Tetrahedron*, vol. 47, No. 36, pp. 7615-7624 (1991).
Osipov, et al: "A radical pathway to α-difluoromethylene containing prolines and α-aminoadipic acids", Tetrahedron Letters 41 (2000) 5659-5662.
Shum, P. W., "A Convenient Method for the Synthesis of Unsymmetrical 3,4-Disubstituted Pyrroles," Tetrahedron Letters, vol. 31(47), pp. 6785-6788 (1990).
Stomach Cancer [online], [retrieved on Aug. 27, 2007]. Retrieved from the Internet, URL; http://www.nlm.nih.gov/medlineplus/print/stomachcancer.html.
Trost, et al, "A [3+2] and [4+3] Cycloaddition Approach to N-Heterocycles via Pd-Catalyzed TMM Reactions with Imines", J. Am. Chem. Soc. 1993, 115, 6636-6645.
Trost, et al "A selectivity control element for palladium-catalyzed trimethylenemethane cycloaddition", J. Am. Chem. Soc. 1991, 113 (23), 9007-9009.
Wolff, Manfred E., "Burger's Medicinal Chemistry, 5th ed., Part I", John Wiley & Sons, 1995, pp. 975-977.
Andersson and Carlsson, "Potassium-competitive acid blockade: a new therapeutic strategy in acid-related diseases." *Pharmacology & Therapeutics* 108 (2005) 294-307.

(56) References Cited

OTHER PUBLICATIONS

Dent, et al., "A Randomized, Comparative Trial of a Potassium-Competitive Acid Blocker (AZD0865) and Esomeprazole for the Treatment of Patients With Nonerosive Reflux Disease." *Am J Gastroenterol* 2008, 103, 20-26.

Fass, et al., "Nonerosive Reflux Disease—Current Concepts and Dilemmas." *Am J Gastroenterol* 2001: 96: 303-314.

Hirschowitz, et al., "Long-term treatment with lansoprazole for patients with Zollinger-Ellison syndrome." *Aliment Pharmacol Ther* 1996; 10; 507-522.

Julapalli and Graham, "Appropriate Use of Intravenous Proton Pump Inhibitors in the Management of Bleeding Peptic Ulcer." *Digestive Diseases and Sciences*, vol. 50, No. 7 (Jul. 2005), pp. 1185-1193.

Kandulski, et al., "Gastric precancerous lesions", *Digestive and Liver Disease* 40 (2008) 619-626.

Katz, et al., "Review article: acid-related disease—what are the unmet clinical needs?" suppression. *Aliment Pharmacol Ther* 23 (Suppl. 2), 9-22, 2006.

Lochhead, et al., "*Helicobacter pylori* infection and gastric cancer." *Best Practice & Research Clinical Gastroenterology* vol. 21, No. 2, pp. 281-297, 2007.

Malfertheiner, et al., "Current concepts in the management of *Helicobacter pylori* infection: the Maastricht III Consensus Report." *Gut* 2007; 56: 772-781.

Martinek, et al., "Non-erosive and erosive gastroesophageal reflux diseases: No difference with regard to reflux pattern and motility abnormalities." *Scandinavian Journal of Gastroenterology*, 2008; 43; 794-800.

Miner, "Review article: physiologic and clinical effects of proton pump inhibitors on non-acidic and acidic gastro-oesophageal reflux." *Aliment Pharmacol Ther* 23 (Suppl. 1), 25-32, 2006.

Morgner, et al., "Esomeprazole: prevention and treatment of NSAI-induced symptoms and ulcers." *Expert Opin. Pharmacother.* (2007) 8(7): 975-988.

Robinson, "Proton pump inhibitors: update on their role in acid-related gastrointestinal diseases." *Int J Clin Pract*, Jun. 2005, 59, 6, 709-715.

Sachs, et al., "Current trends in the treatment of upper gastrointestinal disease." *Best Practice & Research Clinical Gastroenterology* vol. 16, No. 6, pp. 835-849, 2002.

Scarpignato and Pelosini, "Review article: the opportunities and benefits of extended acid suppression." *Aliment Pharmacol Ther* 23 (Suppl. 2), 23-34, 2006.

Schubert and Peura, "Control of Gastric Acid Secretion in Health and Disease." *Gastroenterology* 2008; 134: 1842-1860.

Shi, et al., "Proton pump inhibitors: an update on their clinical use and pharmokinetics." *Eur J Clin Pharmacol* (2008) 64: 935-951.

Suzuki, et al., "*Helicobacter pylori*: present status and future prospects in Japan." *J Gastroenterol* 2007: 42: 1-15.

Talley and Vakil, "Guidelines for the Management of Dyspepsia." *Am J Gastroenterol* 2005: 100: 2324-2337.

Tonini, et al., "Novel therapeutic strategies in acid-related disorders." *Expert Opin. Ther. Patents* (2003) 13(5) 639-649.

van Leerdam and Rauws, "The role of acid suppressants in upper gastrointestinal ulcer bleeding." *Best Practice & Research Clinical Gastroenterology* vol. 15, No. 3, pp. 463-475, 2001.

Vogiatzi, et al., "*Helicobacter pylori* as a Class I carcinogen: Physiopathology and Management Strategies" *Journal of Cellular Biochemistry* 102: 264-273 (2007).

\* cited by examiner

PYRROLE COMPOUNDS

CROSS-REFERENCE TO RELATED APPLICATIONS

This application is a divisional application of U.S. Ser. No. 13/061,078, filed Feb. 25, 2011. U.S. Ser. No. 13/061,078 is the U.S. national phase, pursuant to 35 U.S.C. §371, of PCT international application Ser. No. PCT/JP2009/065279, filed Aug. 26, 2009, designating the United States and published in English on Mar. 4, 2010 as publication WO/2010/024451, which claims priority to Japanese Patent Application Ser. No. 2008-218851, filed Aug. 27, 2008 and Japanese Patent Application Ser. No. 2008-269099, filed Oct. 17, 2008. The entire contents of the aforementioned patent applications are incorporated herein by reference.

TECHNICAL FIELD

The present invention relates to pyrrole compounds having an acid secretion suppressive activity.

BACKGROUND OF THE INVENTION

Proton pump inhibitors represented by omeprazole, which suppress gastric acid secretion for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before onset of action, and about 5 days to exhibit maximum efficacy by consecutive administration. In addition, since the existing proton pump inhibitors show variable treatment effects due to metabolic enzyme polymorphism and drug interaction with medicaments such as diazepam and the like, an improvement has been desired.

As pyrrole compounds having a proton pump inhibitory action, patent reference 1 describes a compound represented by the formula:

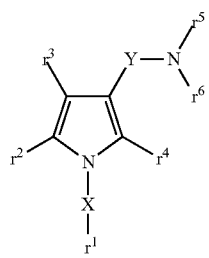

wherein X and Y are the same or different and each is a bond or a spacer having 1 to 20 atoms in the main chain, $r^1$ is an optionally substituted hydrocarbon group or an optionally substituted heterocyclic group, $r^2$, $r^3$ and $r^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $r^5$ and $r^6$ are the same or different and each is a hydrogen atom or an optionally substituted hydrocarbon group. In addition, as a pyrrole compound having a proton pump inhibitory activity, patent document 2 describes a compound represented by the formula

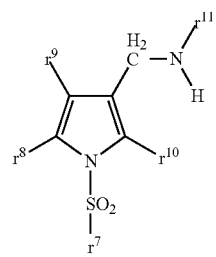

wherein $r^7$ is a monocyclic nitrogen-containing heterocyclic group optionally fused with a benzene ring or heterocycle, the monocyclic nitrogen-containing heterocyclic group optionally fused with a benzene ring or heterocycle optionally has substituent(s), $r^8$ is an optionally substituted $C_{6-14}$ aryl group, an optionally substituted thienyl group or an optionally substituted pyridyl group, $r^9$ and $r^{10}$ are the same or different and each is a hydrogen atom or one of $r^9$ and $r^{10}$ is a hydrogen atom and the other is an optionally substituted lower alkyl group, an acyl group, a halogen atom, a cyano group or a nitro group, and $r^{11}$ is an alkyl group, and the like.

Furthermore, as a therapeutic drug for neoplastic diseases or autoimmune diseases, patent reference 3 describes a compound represented by the formula:

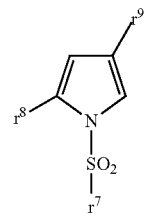

wherein $r^7$ is aryl, aralkyl, heteroaryl or the like, $r^8$ is aryl, heteroaryl or the like, and $r^9$ is aryl, heteroaryl, optionally substituted aminomethyl or the like.

CITATION LIST

Patent Literature

Patent reference 1: WO 2006/036024
Patent reference 2: WO 2007/026916
Patent reference 3: WO 2004/103968

SUMMARY OF THE INVENTION

Problems to be Solved by the Invention

A medicament that effectively suppresses gastric acid secretion as known proton pump inhibitors, which is improved in instability under acidic conditions, dispersion of effects due to metabolic enzyme polymorphism and drug interaction, which are problems of known proton pump inhibitors, is expected to show more superior treatment effect on peptic ulcer, reflux esophagitis and the like. As the situation stands, however, a proton pump inhibitor capable of sufficiently satisfying these requirements has not been found. It is therefore an object of the present invention to provide a compound having a superior acid secretion suppressive effect (particularly, proton pump inhibitory effect), which has been improved in these problems.

Means of Solving the Problems

The present inventors have conducted various studies and found that a compound represented by the formula (I):

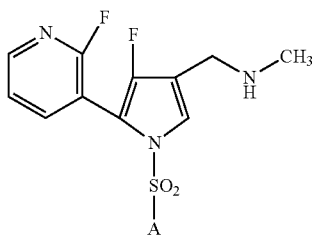

wherein the symbols are to be defined below, or a salt thereof [hereinafter to be sometimes abbreviated as compound (I)] unexpectedly has a very strong proton pump inhibitory effect, and is fully satisfactory as a medicament, which resulted in the completion of the present invention.

Accordingly, the present invention relates to the following.
[1] A compound represented by the formula (I)

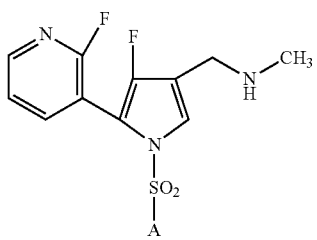

wherein A is a pyridyl group having at least one substituent:

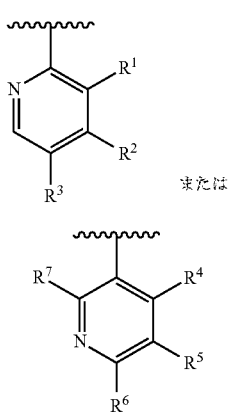

wherein $R^1$, $R^2$ and $R^3$ are each a hydrogen atom, a halogen atom, a $C_{1-6}$ alkyl group optionally substituted by halogen or a $C_{1-6}$ alkoxy group optionally substituted by halogen, $R^4$ and $R^6$ are each a hydrogen atom, a halogen atom or a $C_{1-6}$ alkyl group optionally substituted by halogen, $R^5$ is a hydrogen atom, a halogen atom, a $C_{1-6}$ alkyl group optionally substituted by halogen or a $C_{1-6}$ alkoxy group optionally substituted by halogen, and $R^7$ is a hydrogen atom or a $C_{1-6}$ alkyl group optionally substituted by halogen, or a salt thereof,

[2] the compound of the above-mentioned [1], wherein A is represented by the formula (A-1) wherein $R^1$ and $R^3$ are both hydrogen atoms, $R^2$ is a halogen atom, a $C_{1-6}$ alkyl group optionally substituted by halogen or a $C_{1-6}$ alkoxy group optionally substituted by halogen, or a salt thereof,

[3] the compound of the above-mentioned [2], wherein $R^2$ is a $C_{1-6}$ alkyl group or a $C_{1-6}$ alkoxy group, or a salt thereof,

[4] 1-{4-fluoro-5-(2-fluoropyridin-3-yl)-1-[(4-methylpyridin-2-yl)sulfonyl]-1H-pyrrol-3-yl}-N-methylmethanamine, or a salt thereof,

[5] 1-{4-fluoro-5-(2-fluoropyridin-3-yl)-1-[(5-fluoropyridin-2-yl)sulfonyl]-1H-pyrrol-3-yl}-N-methylmethanamine, or a salt thereof,

[6] 1-{4-fluoro-5-(2-fluoropyridin-3-yl)-1-[(4-methoxypyridin-2-yl)sulfonyl]-1H-pyrrol-3-yl}-N-methylmethanamine, or a salt thereof,

[7] 1-{4-fluoro-5-(2-fluoropyridin-3-yl)-1-[(5-fluoropyridin-3-yl)sulfonyl]-1H-pyrrol-3-yl}-N-methylmethanamine, or a salt thereof,

[8] 1-{4-fluoro-5-(2-fluoropyridin-3-yl)-1-[(6-methylpyridin-3-yl)sulfonyl]-1H-pyrrol-3-yl}-N-methylmethanamine, or a salt thereof,

[9] a prodrug of the compound of the above-mentioned [1] or a salt thereof,

[10] a pharmaceutical composition comprising the compound of the above-mentioned [1] or a salt thereof or a prodrug thereof,

[11] the pharmaceutical composition of the above-mentioned [10], which is an acid secretion inhibitor,

[12] the pharmaceutical composition of the above-mentioned [10], which is a potassium-competitive acid blocker,

[13] the pharmaceutical composition of the above-mentioned [10], which is an agent for the prophylaxis or treatment of peptic ulcer, Zollinger-Ellison syndrome, gastritis, reflux esophagitis, symptomatic gastroesophageal reflux disease (symptomatic GERD), Barrett's esophagus, functional dyspepsia, gastric cancer, stomach MALT lymphoma, or ulcer caused by non-steroidal anti-inflammatory drug, gastric hyperacidity or ulcer due to postoperative stress; or an inhibitor of upper gastrointestinal bleeding due to peptic ulcer, acute stress ulcer, hemorrhagic gastritis or invasive stress,

[14] a method for treating or preventing peptic ulcer, Zollinger-Ellison syndrome, gastritis, reflux esophagitis, symptomatic gastroesophageal reflux disease (symptomatic GERD), Barrett's esophagus, functional dyspepsia, gastric cancer, stomach MALT lymphoma, or ulcer caused by non-steroidal anti-inflammatory drug, gastric hyperacidity or ulcer due to postoperative stress; or a method of inhibiting upper gastrointestinal bleeding due to peptic ulcer, acute stress ulcer, hemorrhagic gastritis or invasive stress, which comprises administering an effective amount of the compound of the above-mentioned [1] or a salt thereof or a prodrug thereof to a mammal,

[15] use of the compound of the above-mentioned [1] or a salt thereof or a prodrug thereof for the production of an agent for the prophylaxis or treatment of peptic ulcer, Zollinger-Ellison syndrome, gastritis, reflux esophagitis, symptomatic gastroesophageal reflux disease (symptomatic GERD), Barrett's esophagus, functional dyspepsia, gastric cancer, stomach MALT lymphoma, or ulcer caused by non-steroidal anti-inflammatory drug, gastric hyperacidity or ulcer due to postoperative stress; or an inhibitor of upper gastrointestinal bleeding due to peptic ulcer, acute stress ulcer, hemorrhagic gastritis or invasive stress, and

[16] the compound of the above-mentioned [1], wherein A is a pyridyl group having at least one substituent, the formula (A-1) or the formula (A-2) wherein one of $R^1$ and $R^3$ is a halogen atom, a $C_{1-6}$ alkyl group optionally substituted by halogen or a $C_{1-6}$ alkoxy group optionally substituted by halogen, and the other is a hydrogen atom, a halogen atom, a $C_{1-6}$ alkyl group optionally substituted by halogen or a $C_{1-6}$ alkoxy group optionally substituted by halogen, $R^2$ is a hydrogen atom, a halogen atom, a $C_{1-6}$ alkyl group optionally substituted by halogen or a $C_{1-6}$ alkoxy group optionally substituted by halogen, $R^4$ and $R^6$ are each a hydrogen atom, a halogen atom or a $C_{1-6}$ alkyl group optionally substituted by halogen, $R^5$ is a hydrogen atom, a halogen atom, a $C_{1-6}$ alkyl group optionally substituted by halogen or a $C_{1-6}$ alkoxy group optionally substituted by halogen, and $R^7$ is a hydrogen atom or a $C_{1-6}$ alkyl group optionally substituted by halogen, or a salt thereof.

Effect of the Invention

Compound (I) of the present invention shows a superior proton pump inhibitory effect. Conventional proton pump inhibitors such as omeprazole, lansoprazole and the like are converted to active forms in an acidic environment of gastric parietal cells and form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ competitive manner, and consequently suppresses acid secretion. Therefore, it is sometimes called a potassium-competitive acid blocker (P-CAB), or an acid pump antagonist (APA). Compound (I) rapidly exhibits the action and shows the maximum efficacy from the initial administration. Furthermore, its metabolism is less influenced by metabolic polymorphism and variation of efficacy among patients is small. In addition, it has been found that compound (I) is designed to have a characteristic chemical structure wherein (i) the substituent at the 5-position of pyrrole ring is a 2-F-3-pyridyl group, (ii) the substituent at the 4-position of pyrrole ring is a fluorine atom, and (iii) the 1-position of pyrrole ring is a 2-pyridylsulfonyl group or 3-pyridylsulfonyl group having at least one substituent, and such chemical structure is conducive to a strong proton pump inhibitory activity, and significantly decreases cytotoxicity. Furthermore, it is characterized in that substitution of the 4-position of pyrrole ring by a fluorine atom in compound (I) lowers basicity (pKa value) of methylaminomethyl moiety due to an electron withdrawing effect of the fluorine atom, and decreases the risk of toxicity expression derived from strong basicity, and that introduction of at least one substituent into 2-pyridyl group or 3-pyridyl group in A of compound (I) controls the duration of action optimally. Hence, the present invention can provide a clinically useful agent for the prophylaxis or treatment of peptic ulcer (e.g., gastric ulcer, duodenal ulcer, anastomotic ulcer, ulcer caused by non-steroidal anti-inflammatory drug, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia, gastric cancer, stomach MALT lymphoma or hyperacidity; or a suppressant of upper gastrointestinal bleeding due to peptic ulcer, acute stress ulcer, hemorrhagic gastritis or invasive stress; and the like. Since compound (I) shows low toxicity and is superior in water-solubility, in vivo kinetics and efficacy exhibition, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, onset of suppression of gastric acid secretion is rapid, and symptoms such as pain and the like can be alleviated rapidly.

DETAILED DESCRIPTION OF THE INVENTION

Figure 1:
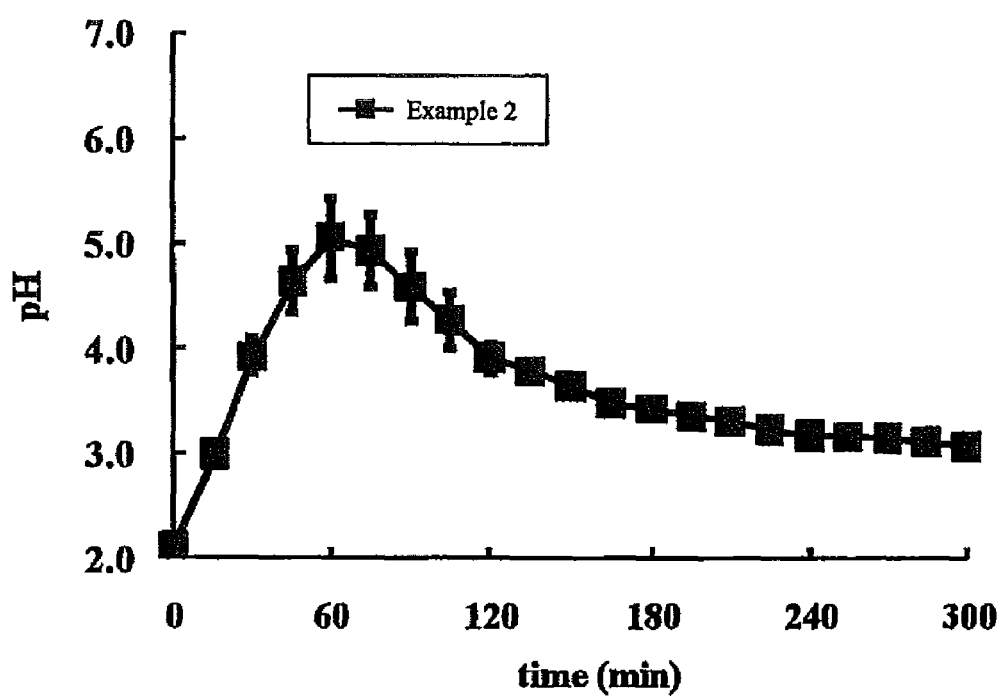
FIG. 1 shows results of perfusate pH measurement test in anesthetized rat stomach perfusion model in Example 2.

In the present specification, examples of the "halogen atom" and "halogen" include a fluorine atom, a chlorine atom, a bromine atom and an iodine atom. In the formula (I), A is a pyridyl group having at least one substituent. Examples of the "pyridyl group having at least one substituent" for A include a group represented by the formula

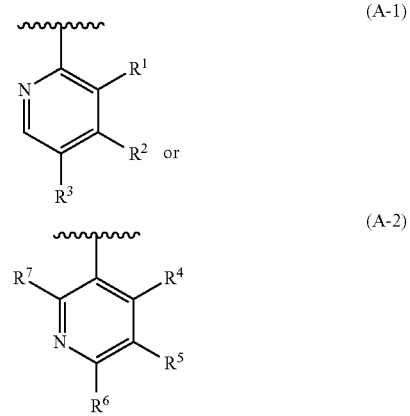

wherein $R^1$, $R^2$ and $R^3$ are each a hydrogen atom, a halogen atom, a $C_{1-6}$ alkyl group optionally substituted by halogen or a $C_{1-6}$ alkoxy group optionally substituted by halogen, $R^4$ and $R^6$ are each a hydrogen atom, a halogen atom or a $C_{1-6}$ alkyl group optionally substituted by halogen, $R^5$ is a hydrogen atom, a halogen atom, a $C_{1-6}$ alkyl group optionally substituted by halogen or a $C_{1-6}$ alkoxy group optionally substituted by halogen, and $R^7$ is a hydrogen atom or a $C_{1-6}$ alkyl group optionally substituted by halogen. By "having at least one substituent" is meant that at least one of $R^1$, $R^2$ and $R^3$ in the partial structure (A-1) is not a hydrogen atom, and at least one of $R^4$, $R^5$, $R^6$ and $R^7$ in the partial structure (A-2) is not a hydrogen atom.

The "$C_{1-6}$ alkyl group optionally substituted by halogen" for $R^1$, $R^2$, $R^3$, $R^4$, $R^5$, $R^6$ or $R^7$ is a $C_{1-6}$ alkyl group optionally having 1 to 5 (preferably 1 to 3) halogen atoms (e.g., fluorine atom, chlorine atom, bromine atom, iodine atom), and examples thereof include methyl, ethyl, n-propyl, isopropyl, n-butyl, isobutyl, sec-butyl, tert-butyl, n-pentyl, sec-pentyl, isopentyl, neopentyl, n-hexyl, isohexyl, trifluoromethyl and the like.

The "$C_{1-6}$ alkoxy group optionally substituted by halogen" for $R^1$, $R^2$, $R^3$ or $R^5$ is a $C_{1-6}$ alkoxy group optionally having 1 to 5 (preferably 1 to 3) halogen atoms (e.g., fluorine atom, chlorine atom, bromine atom, iodine atom), and examples thereof include methoxy, ethoxy, propoxy, isopropoxy, butoxy, isobutoxy, sec-butoxy, pentyloxy, hexyloxy, fluoromethoxy, trifluoromethoxy and the like.

$R^1$ is preferably a hydrogen atom or a $C_{1-6}$ alkyl group optionally substituted by halogen (e.g., methyl, ethyl). $R^2$ is preferably a hydrogen atom, a $C_{1-6}$ alkyl group optionally substituted by halogen (e.g., methyl, ethyl), a $C_{1-6}$ alkoxy group optionally substituted by halogen (e.g., methoxy, ethoxy). $R^3$ is preferably a hydrogen atom, a halogen atom (e.g., fluorine atom, chlorine atom, bromine atom, iodine atom), a $C_{1-6}$ alkoxy group optionally substituted by halogen (e.g., methoxy, ethoxy). $R^4$ is preferably a hydrogen atom, a $C_{1-6}$ alkyl group optionally substituted by halogen (e.g., methyl, ethyl). $R^5$ is preferably a hydrogen atom, a halogen atom (e.g., fluorine atom, chlorine atom, bromine atom, iodine atom), a $C_{1-6}$ alkyl group optionally substituted by halogen (e.g., methyl, ethyl), a $C_{1-6}$ alkoxy group optionally substituted by halogen (e.g., methoxy, ethoxy). $R^6$ is preferably a hydrogen atom, a $C_{1-6}$ alkyl group optionally substituted by halogen (e.g., methyl, ethyl). $R^7$ is preferably a hydrogen atom, a $C_{1-6}$ alkyl group optionally substituted by halogen (e.g., methyl, ethyl).

$R^1$ is particularly preferably a hydrogen atom or a $C_{1-6}$ alkyl group. $R^2$ is particularly preferably a hydrogen atom, a $C_{1-6}$ alkyl group or a $C_{1-6}$ alkoxy group. $R^3$ is particularly preferably a hydrogen atom, a halogen atom or a $C_{1-6}$ alkoxy group. $R^4$ is particularly preferably a hydrogen atom or a $C_{1-6}$ alkyl group. $R^5$ is particularly preferably a hydrogen atom, a halogen atom or a $C_{1-6}$ alkyl group. $R^6$ is particularly preferably a hydrogen atom or a $C_{1-6}$ alkyl group. $R^7$ is particularly preferably a hydrogen atom or a $C_{1-6}$ alkyl group.

In the formula (I), A can be classified into the following embodiments.

(i) A is represented by the formula (A-1) wherein both $R^1$ and $R^3$ are hydrogen atoms, $R^2$ is a halogen atom, a $C_{1-6}$ alkyl group optionally substituted by halogen or a $C_{1-6}$ alkoxy group optionally substituted by halogen.

(ii) A is a pyridyl group having at least one substituent, represented by the formula (A-1) or represented by the formula (A-2), wherein one of $R^1$ and $R^3$ is a halogen atom, a $C_{1-6}$ alkyl group optionally substituted by halogen or a $C_{1-6}$ alkoxy group optionally substituted by halogen, and the other is a hydrogen atom, a halogen atom, a $C_{1-6}$ alkyl group optionally substituted by halogen or a $C_{1-6}$ alkoxy group optionally substituted by halogen, $R^2$ is a hydrogen atom, a halogen atom, a $C_{1-6}$ alkyl group optionally substituted by halogen or a $C_{1-6}$ alkoxy group optionally substituted by halogen, $R^4$ and $R^6$ are each a hydrogen atom, a halogen atom or a $C_{1-6}$ alkyl group optionally substituted by halogen, $R^5$ is a hydrogen atom, a halogen atom, a $C_{1-6}$ alkyl group optionally substituted by halogen or a $C_{1-6}$ alkoxy group optionally substituted by halogen, and $R^7$ is a hydrogen atom or a $C_{1-6}$ alkyl group optionally substituted by halogen.

Another preferable embodiment of A in the formula (I) is the formula

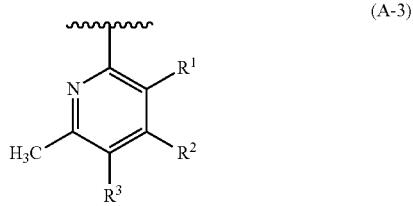

(A-3)

wherein $R^1$, $R^2$ and $R^3$ are as defined above, and show preferable embodiments of the corresponding substituents in the formula (I). The pyridyl group of a partial structure (A-3) has, besides methyl group, at least one substituent $R^1$, $R^2$ or $R^3$. In the partial structure (A-3), at least one of $R^1$, $R^2$ and $R^3$ is not a hydrogen atom.

As the "pyridyl group having at least one substituent" for A, preferred is the formula

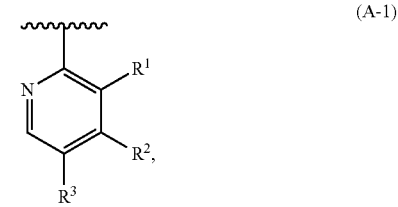

(A-1)

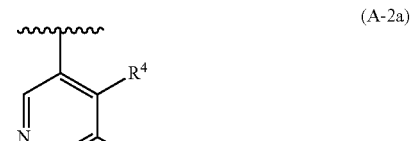

(A-2a)

or

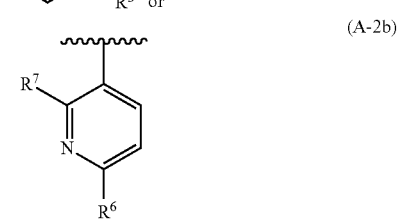

(A-2b)

wherein $R^1$, $R^2$, $R^3$, $R^4$, $R^5$, $R^6$ and $R^7$ are as defined above, and show preferable embodiments of the corresponding substituents in the formula (I). In a partial structure (A-2a), at least one of $R^4$ and $R^5$ is not a hydrogen atom, and in the partial structure (A-2b), at least one of $R^6$ and $R^7$ is not a hydrogen atom.

Particularly preferable embodiment of compound (I) is a compound represented by the following formula (Ia) or (Ib) or a salt thereof.

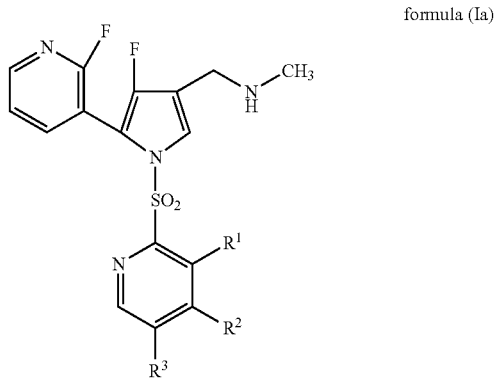

formula (Ia)

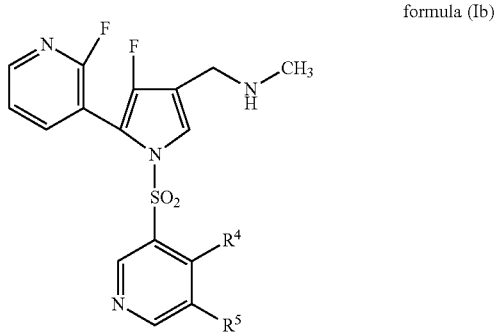

formula (Ib)

Here, preferable embodiments of each substituent in the formulas (Ia) and (Ib) are those of the corresponding substituent in the formula (I).

Particularly preferable other embodiments of compound (I) are compounds represented by the following formula (Ia-1), the formula (Ia-2), the formula (Ib) and the formula (Ic) and salts thereof.

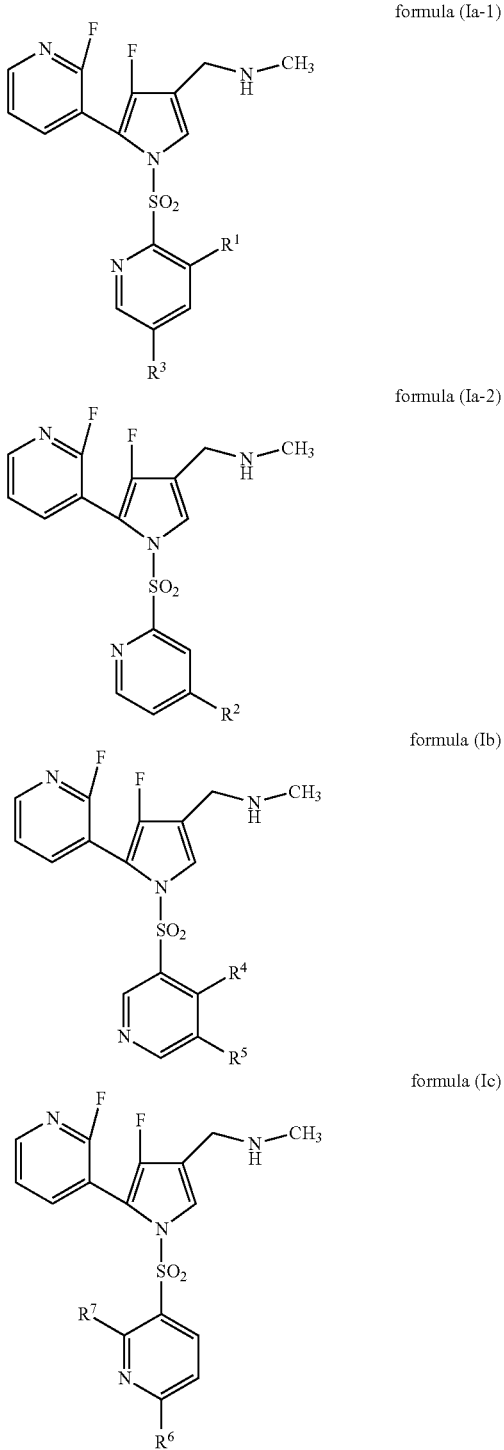

formula (Ia-1)

formula (Ia-2)

formula (Ib)

formula (Ic)

Here, preferable embodiments of each substituent in the formulas (Ia-1), the formula (Ia-2), the formula (Ib) and the formula (Ic) are those of the corresponding substituent in the formula (I). However, at least one of $R^1$ and $R^3$ in the formula (Ia-1) is not a hydrogen atom, $R^2$ in the formula (Ia-2) is not a hydrogen atom, at least one of $R^4$ and $R^5$ in the formula (Ib) is not a hydrogen atom, and at least one of $R^6$ and $R^7$ in the formula (Ic) is not a hydrogen atom.

Specifically, $R^1$ and $R^3$ in the formula (Ia-1) are the same or different and each is a hydrogen atom, a halogen atom, a $C_{1-6}$ alkyl group optionally substituted by halogen or a $C_{1-6}$ alkoxy group optionally substituted by halogen. Preferred as $R^1$ of the formula (Ia-1) is a hydrogen atom or a $C_{1-6}$ alkyl group optionally substituted by halogen, particularly preferably a hydrogen atom or a $C_{1-6}$ alkyl group. Preferred as $R^3$ of the formula (Ia-1) is a hydrogen atom, a halogen atom or a $C_{1-6}$ alkoxy group optionally substituted by halogen, particularly preferably a hydrogen atom, a halogen atom or a $C_{1-6}$ alkoxy group.

$R^2$ of the formula (Ia-2) is a halogen atom, a $C_{1-6}$ alkyl group optionally substituted by halogen or a $C_{1-6}$ alkoxy group optionally substituted by halogen. Preferred as $R^2$ of the formula (Ia-2) is a $C_{1-6}$ alkyl group optionally substituted by halogen or a $C_{1-6}$ alkoxy group optionally substituted by halogen, particularly preferably a $C_{1-6}$ alkyl group or a $C_{1-6}$ alkoxy group.

$R^4$ of the formula (Ib) is a hydrogen atom, a halogen atom or a $C_{1-6}$ alkyl group optionally substituted by halogen. Preferred as $R^4$ is a hydrogen atom or a $C_{1-6}$ alkyl group optionally substituted by halogen, particularly preferably a hydrogen atom or a $C_{1-6}$ alkyl group.

$R^5$ of the formula (Ib) is a hydrogen atom, a halogen atom, a $C_{1-6}$ alkyl group optionally substituted by halogen or a $C_{1-6}$ alkoxy group optionally substituted by halogen. Preferred as $R^5$ is a hydrogen atom, a halogen atom or a $C_{1-6}$ alkyl group optionally substituted by halogen, particularly preferably a hydrogen atom, a halogen atom or a $C_{1-6}$ alkyl group.

$R^6$ of the formula (Ic) is a hydrogen atom, a halogen atom or a $C_{1-6}$ alkyl group optionally substituted by halogen. Preferred as $R^6$ is a hydrogen atom or a $C_{1-6}$ alkyl group optionally substituted by halogen, particularly preferably a hydrogen atom or a $C_{1-6}$ alkyl group.

$R^7$ of the formula (Ic) is a hydrogen atom or a $C_{1-6}$ alkyl group optionally substituted by halogen. Preferred as $R^7$ is a hydrogen atom or a $C_{1-6}$ alkyl group optionally substituted by halogen, particularly preferably a hydrogen atom or a $C_{1-6}$ alkyl group.

Among those mentioned above, the formula (Ia-2) is particularly preferable.

Of compounds (I), the following compounds are preferable.

1-{4-Fluoro-5-(2-fluoropyridin-3-yl)-1-[(3-methylpyridin-2-yl)sulfonyl]-1H-pyrrol-3-yl}-N-methylmethanamine or a salt thereof, 1-{4-fluoro-5-(2-fluoropyridin-3-yl)-1-[(4-methylpyridin-2-yl)sulfonyl]-1H-pyrrol-3-yl}-N-methylmethanamine or a salt thereof, 1-{4-fluoro-5-(2-fluoropyridin-3-yl)-1-[(5-fluoropyridin-2-yl)sulfonyl]-1H-pyrrol-3-yl}-N-methylmethanamine or a salt thereof, 1-{4-fluoro-5-(2-fluoropyridin-3-yl)-1-[(4-methoxypyridin-2-yl)sulfonyl]-1H-pyrrol-3-yl}-N-methylmethanamine or a salt thereof, 1-{4-fluoro-5-(2-fluoropyridin-3-yl)-1-[(5-fluoropyridin-3-yl)sulfonyl]-1H-pyrrol-3-yl}-N-methylmethanamine or a salt thereof, 1-{4-fluoro-5-(2-fluoropyridin-3-yl)-1-[(4-methylpyridin-3-yl)sulfonyl]-1H-pyrrol-3-yl}-N-methylmethanamine or a salt thereof, 1-{4-fluoro-5-(2-fluoropyridin-3-yl)-1-[(5-methylpyridin-3-yl)sulfonyl]-1H-pyrrol-3-yl}-N-methylmethanamine or a salt thereof,
1-{4-fluoro-5-(2-fluoropyridin-3-yl)-1-[(6-methylpyridin-3-yl)sulfonyl]-1H-pyrrol-3-yl}-N-methylmethanamine or a salt thereof,
1-{4-fluoro-5-(2-fluoropyridin-3-yl)-1-[(2-methylpyridin-3-yl)sulfonyl]-1H-pyrrol-3-yl}-N-methylmethanamine or a salt thereof,
1-{4-fluoro-5-(2-fluoropyridin-3-yl)-1-[(5-methoxypyridin-2-yl)sulfonyl]-1H-pyrrol-3-yl}-N-methylmethanamine or a salt thereof,
1-{1-[(5-chloropyridin-3-yl)sulfonyl]-4-fluoro-5-(2-fluoropyridin-3-yl)-1H-pyrrol-3-yl}-N-methylmethanamine or a salt thereof,
1-{4-fluoro-1-[(5-fluoro-6-methylpyridin-2-yl)sulfonyl]-5-(2-fluoropyridin-3-yl)-1H-pyrrol-3-yl}-N-methylmethanamine or a salt thereof,
1-{4-fluoro-1-[(5-fluoro-4-methylpyridin-2-yl)sulfonyl]-5-(2-fluoropyridin-3-yl)-1H-pyrrol-3-yl}-N-methylmethanamine or a salt thereof,
1-{4-fluoro-1-[(5-fluoro-4-methoxypyridin-2-yl)sulfonyl]-5-(2-fluoropyridin-3-yl)-1H-pyrrol-3-yl}-N-methyl-methanamine or a salt thereof,
1-{4-fluoro-5-(2-fluoropyridin-3-yl)-1-[(5-methoxypyridin-3-yl)sulfonyl]-1H-pyrrol-3-yl}-N-methylmethanamine or a salt thereof,
1-{4-fluoro-1-[(5-fluoro-6-methylpyridin-3-yl)sulfonyl]-5-(2-fluoropyridin-3-yl)-1H-pyrrol-3-yl}-N-methylmethanamine or a salt thereof,
1-{1-[(4,6-dimethylpyridin-2-yl)sulfonyl]-4-fluoro-5-(2-fluoropyridin-3-yl)-1H-pyrrol-3-yl}-N-methylmethanamine or a salt thereof,
1-{1-[(5-chloropyridin-2-yl)sulfonyl]-4-fluoro-5-(2-fluoropyridin-3-yl)-1H-pyrrol-3-yl}-N-methylmethanamine or a salt thereof,
1-{1-[(5,6-dimethylpyridin-2-yl)sulfonyl]-4-fluoro-5-(2-fluoropyridin-3-yl)-1H-pyrrol-3-yl}-N-methylmethanamine or a salt thereof,
1-{1-[(4,5-dimethylpyridin-2-yl)sulfonyl]-4-fluoro-5-(2-fluoropyridin-3-yl)-1H-pyrrol-3-yl}-N-methylmethanamine or a salt thereof, and
1-{4-fluoro-5-(2-fluoropyridin-3-yl)-1-[(5-fluoropyridin-3-yl)sulfonyl]-1H-pyrrol-3-yl}-N-methylmethanamine or a salt thereof.

As compound (I), the following compounds are particularly preferable.
1-{4-Fluoro-5-(2-fluoropyridin-3-yl)-1-[(4-methylpyridin-2-yl)sulfonyl]-1H-pyrrol-3-yl}-N-methylmethanamine or a salt thereof,
1-{4-fluoro-5-(2-fluoropyridin-3-yl)-1-[(5-fluoropyridin-2-yl)sulfonyl]-1H-pyrrol-3-yl}-N-methylmethanamine or a salt thereof,
1-{4-fluoro-5-(2-fluoropyridin-3-yl)-1-[(4-methoxypyridin-2-yl)sulfonyl]-1H-pyrrol-3-yl}-N-methylmethanamine or a salt thereof,
1-{4-fluoro-5-(2-fluoropyridin-3-yl)-1-[(5-fluoropyridin-3-yl)sulfonyl]-1H-pyrrol-3-yl}-N-methylmethanamine or a salt thereof, and
1-{4-fluoro-5-(2-fluoropyridin-3-yl)-1-[(6-methylpyridin-3-yl)sulfonyl]-1H-pyrrol-3-yl}-N-methylmethanamine or a salt thereof.

Examples of the salt of compound (I) include metal salt, ammonium salt, salts with organic bases, salts with inorganic bases, salts with organic acids, salts with basic or acidic amino acids and the like. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like. Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salt and the like can be mentioned; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

The production methods of compound (I) in the present invention are explained. The compounds (II)-(XXXIII) in the formula may form salts, and as such salts, for example, those similar to the salts of compound (I) can be mentioned. While the compounds obtained in respective steps can be used for the next reaction in the form of a reaction mixture or a crude product, they can also be easily isolated and purified from the reaction mixture by a known separation and purification means, such as recrystallization, distillation, chromatography and the like.

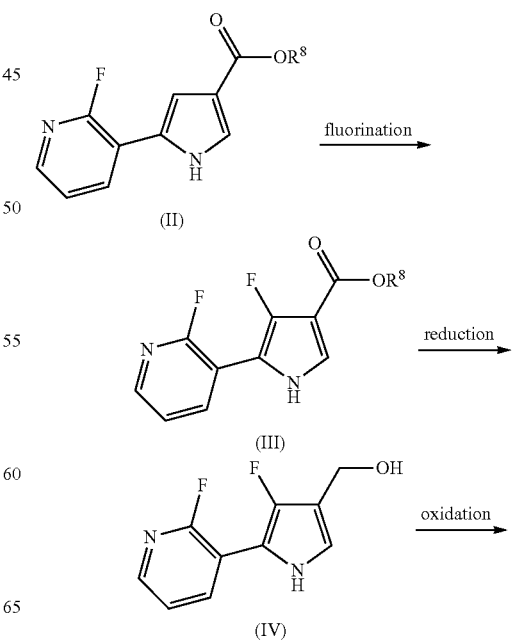

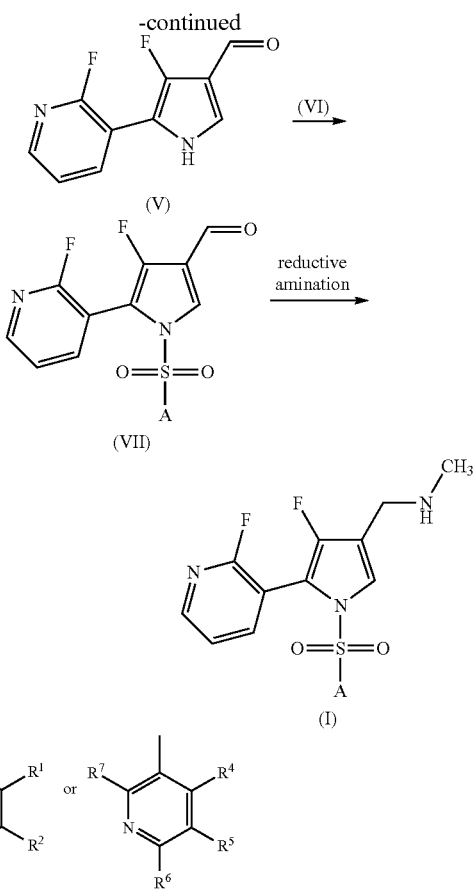

Compound (II) wherein R⁸ is a $C_{1-4}$ alkyl group such as methyl, ethyl, propyl, isopropyl, butyl and the like can be produced according to a method known per se, such as the method described in Chem. Pharm. Bull., vol. 49, p. 1406 (2001), Tetrahedron Letters, vol. 35, p. 5989 (1994) and the like or a method analogous thereto.

Compound (III) wherein each symbol is as defined above can be produced by fluorinating compound (II) with a fluorinating reagent such as N-fluoropyridinium salt, xenon difluoride and the like. The amount of the fluorinating reagent to be used is 0.75-10 equivalents, preferably 1-5 equivalents, relative to compound (II). This reaction is advantageously carried out using a solvent inert to the reaction. While the solvent is not particularly limited as long as the reaction proceeds, hydrocarbons such as benzene, toluene and the like, tetrahydrofuran, diethyl ether, acetonitrile and the like or a mixed solvent thereof and the like is preferable. While the reaction time varies depending on the reagents and solvent to be used, it is generally 10 min to 24 hr, preferably 30 min to 12 hr. The reaction temperature is generally −78° C. to 100° C., preferably −20° C. to 60° C. In addition, it is possible to introduce a fluorine group by stepwise reactions, for example, bromination with N-bromosuccinimide (NBS) and the like, followed by conversion to a fluorine group by substitution reaction.

Compound (IV) can be produced by reducing compound (III) with a reducing agent such as lithium aluminum hydride, diisobutylaluminum hydride, sodium borohydride, calcium borohydride and the like. As the reducing agent, diisobutylaluminum hydride is particularly preferable. The amount of the reducing agent to be used is 0.75-10 equivalents, preferably 1-5 equivalents, relative to compound (III).

This reaction is advantageously carried out using a solvent inert to the reaction. While the solvent is not particularly limited as long as the reaction proceeds, solvents such as hydrocarbons such as benzene, toluene and the like, ethers such as tetrahydrofuran, diethyl ether, etc. and the like and a mixed solvent thereof and the like are preferable. While the reaction time varies depending on the reagents and solvents to be used, it is generally 10 min to 24 hr, preferably 30 min to 8 hr. The reaction temperature is generally −78° C. to 100° C., preferably −78° C. to 25° C.

Compound (V) can be produced by reacting compound (IV) with an oxidant such as chromic acid-pyridine complex, pyridinium chlorochromate, manganese dioxide, sulfur trioxide-pyridine complex, tetra-n-propylammonium perruthenate and the like. As the oxidant, manganese dioxide, sulfur trioxide-pyridine complex or tetra-n-propylammonium perruthenate is preferable. This oxidation reaction can be performed, for example, according to the method described in Synthesis, p. 639 (1994).

Compound (VII) can be produced by reacting compound (V) with a compound represented by the formula (VI)

$$A-\overset{\overset{O}{\|}}{\underset{\underset{O}{\|}}{S}}-X \quad (VI)$$

wherein X is a halogen atom such as a fluorine atom, a chlorine atom and the like, and the other symbol is as defined above. The amount of compound (VI) to be used is 0.75-10 mol, preferably 1-3 mol, per 1 mol of compound (V).

This reaction is advantageously carried out using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, acetonitrile and the like or a mixed solvent thereof and the like are preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is 0.8 to 10 mol, preferably 1 to 5 mol, per 1 mol of compound (V). The reaction can also be carried out and is advantageous in the co-presence of a crown ether. As the crown ether, for example, 15-crown-5-ether, 18-crown-6-ether and the like can be mentioned. The amount of the crown ether to be used is 0.01 to 10 mol, preferably 1 to 5 mol, per 1 mol of compound (V). While the reaction time varies depending on the reagents and solvent to be used, it is generally 1 min to 48 hr, preferably 10 min to 8 hr. The reaction temperature is generally −20° C. to 100° C., preferably 0° C. to 50° C.

Compound (I) wherein each symbol is as defined above can be produced using compound (VII) and methylamine or a salt thereof, by a reductive amination reaction analogous to the method described in Jikken Kagaku Koza (Courses in Experimental Chemistry), vol. 14-III, p. 1380-1385 (published by MARUZEN CO., LTD.) and the like. In addition, compound (II) can also be produced according to the following method, and compound (I) can be produced using a method similar to the method described above.

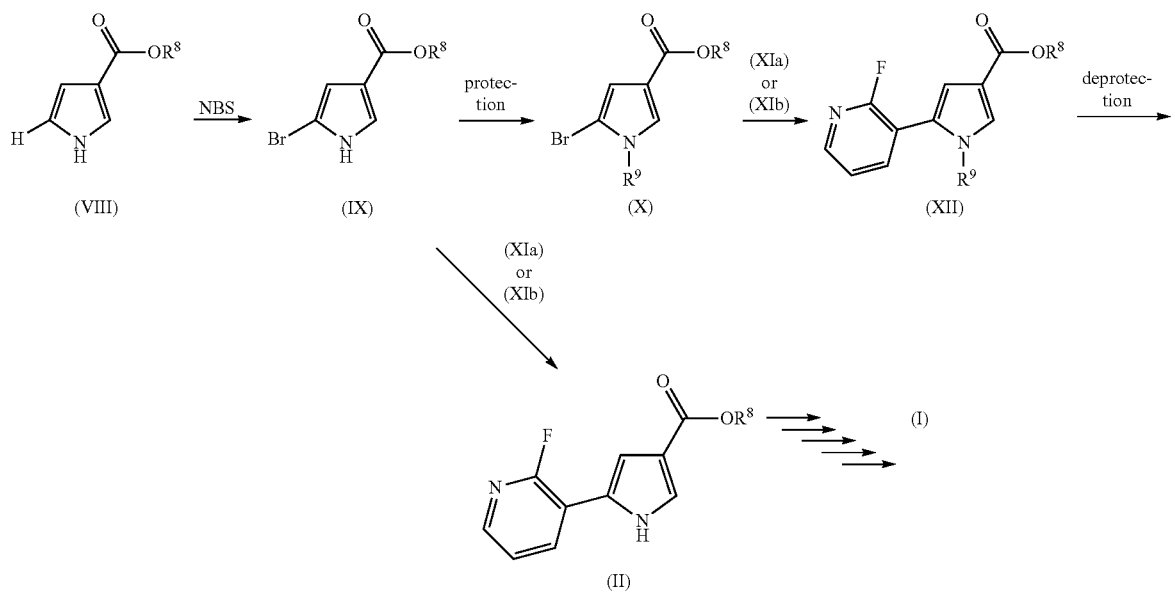

Compound (VIII) wherein each symbol is as defined above can be produced according to a method known per se, for example, the methods described in Tetrahedron Letters, vol. 13, p. 5337 (1972), Heterocycles, vol. 7, p. 77 (1977), Chem. Pharm. Bull., vol. 27, p. 2857 (1979), J. Org. Chem., vol. 62, p. 2649 (1997) and the like, or a method analogous thereto.

Compound (IX) wherein each symbol is as defined above can be produced by reacting compound (VIII) with N-bromosuccinimide (NBS). N-Bromosuccinimide (NBS) is preferably used in about one equivalent relative to compound (VIII), and the reaction is preferably carried out under an inert gas atmosphere such as nitrogen, argon and the like.

This reaction is advantageously carried out using a solvent inert to the reaction. While the solvent is not particularly limited as long as the reaction proceeds, solvents such as ethers (e.g., tetrahydrofuran, diethyl ether and the like), amides (e.g., N,N-dimethylformamide, N,N-dimethylacetamide and the like) and the like, a mixed solvent thereof and the like are preferable. While the reaction time varies depending on the reagents and solvent to be used, it is generally 10 min to 24 hr, preferably 5 to 12 hr. The reaction temperature is generally −78° C. to 80° C., preferably −78° C. to 30° C.

Addition of a base is sometimes effective for the reaction. While the base to be used is not limited as long as the reaction proceeds, organic bases such as pyridine, picoline, lutidine and the like, and the like can be mentioned. The amount of the organic base to be used is 0.001 to 10 equivalents, preferably 0.001 to 0.1 equivalent, per compound (VIII).

Compound (X) wherein $R^9$ is a pyrrole-protecting group and other symbols are as defined above can be produced by protecting pyrrole nitrogen of compound (IX). The pyrrole-protecting group is not particularly limited, and examples thereof include a tert-butoxycarbonyl group (BOC group), a benzyloxycarbonyl group (Cbz group), an aryl or a heteroarylsulfonyl group, a benzyl group, a triisopropylsilyl group and the like.

This protection reaction can be performed according to a method known per se, for example, a method analogous to the method described in Protective Groups in Organic Synthesis, $3^{rd}$ Ed., Theodora W. Greene, Peter G. M. Wuts, pp. 494-653, Wiley-Interscience (1999) and the like.

Compound (XII) wherein each symbol is as defined above can be produced by reacting compound (X) with a compound represented by the formula (XIa)

wherein each symbol is as defined above, or various ester derivatives of the formula (XIa) according to the method described in Synthetic Communications, vol. 11, page 513 (1981), or a method analogous thereto. In addition, can be produced by reacting compound (X) with a compound represented by the formula (XIb)

wherein R is an alkyl group or an aryl group, according to the method described in Synthesis, vol. 7, pages 564-565 (1986) or a method analogous thereto. Examples of the "alkyl group" for R include a methyl group and an n-butyl group, and examples of the "aryl group" include a phenyl group.

Compound (II) wherein each symbol is as defined above can be produced from compound (IX) according to a method similar to the method for producing compound (XII) from compound (X). Alternatively, compound (II) can be produced from compound (XII) by a method known per se, for example, the method described in Protective Groups in Organic Synthesis, $3^{rd}$ Ed., Theodora W. Greene, Peter G. M. Wuts, pp. 494-653, Wiley-Interscience (1999), and the like, by removing a pyrrole nitrogen-protecting group. In addition, compound (I) can also be produced according to the following method.

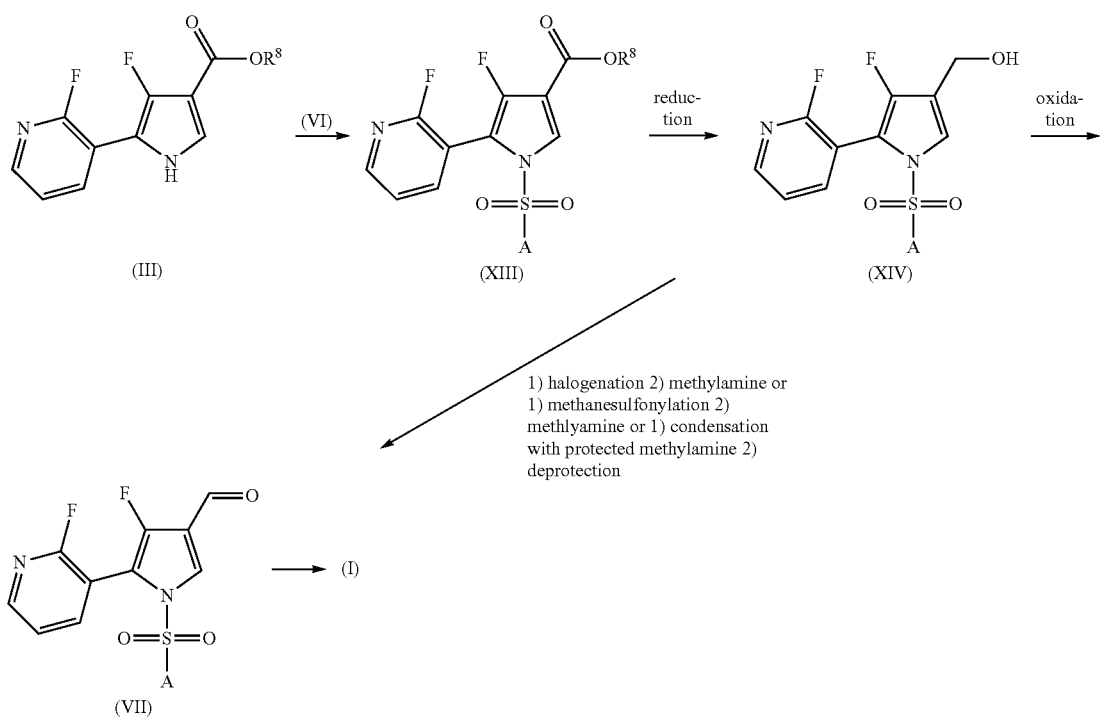

Compound (XIII) wherein each symbol is as defined above can be produced from compound (III) according to a method similar to the method for producing compound (VII) from compound (V).

Compound (XIV) wherein each symbol is as defined above can be produced from compound (XIII) according to a method similar to the method for producing compound (IV) from compound (III).

Compound (VII) wherein each symbol is as defined above can be produced from compound (XIV) according to a method similar to the method for producing compound (V) from compound (IV).

Compound (I) can be produced from compound (VII) by a method similar to the method described above. Alternatively, compound (I) can also be produced from compound (XIV) according to a method including reacting methylamine via halogenation and methanesulfonylation, a method including condensing with methylamine protected by Boc, etc., followed by deprotection and the like. In addition, compound (I) can also be produced according to the following method.

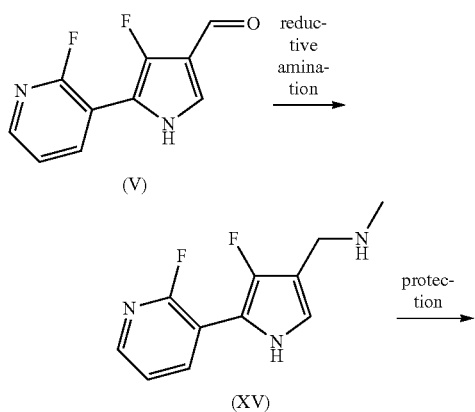

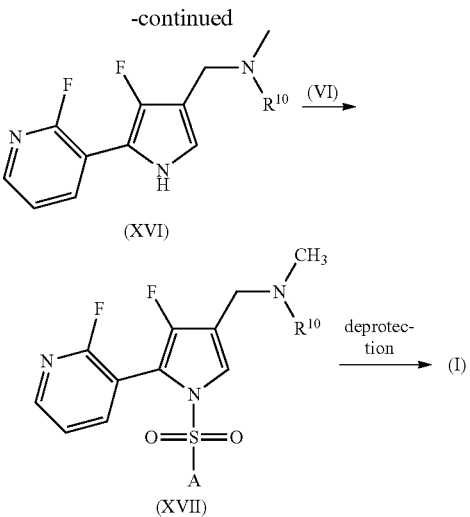

Compound (XV) as defined above can be produced from compound (V) according to a method similar to the method for producing compound (I) from compound (VII).

Compound (XVI) wherein $R^{10}$ is an amino-protecting group can be produced by protecting the amino group of compound (XV). Examples of the amino-protecting group include, but is not particularly limited to, a tert-butoxycarbonyl group (BOC group), a benzyloxycarbonyl group (Cbz group), a 2,4-dimethoxybenzyl group and the like. This protection reaction can be carried out according to a method known per se, for example, the method described in Protective Groups in Organic Synthesis, $3^{rd}$ Ed., Theodora W. Greene, Peter G. M. Wuts, pp. 494-653, Wiley-Interscience (1999) and the like.

Compound (XVII) wherein each symbol is as defined above can be produced from compound (XVI) according to a method similar to the method for producing compound (VII) from compound (V).

Compound (I) can be produced by removing the amino-protecting group from compound (XVII) by a method known per se, for example, the method described in Protective Groups in Organic Synthesis, 3rd Ed., Theodora W. Greene, Peter G. M. Wuts, pp. 494-653, Wiley-Interscience (1999) and the like. Compound (V) can also be produced by the following method. Furthermore, compound (I) can be produced using a method similar to the method described above.

compound (III) from compound (II). In addition, compound (V) can also be produced according to the following method. Further, compound (I) can be produced using a method similar to the method described above.

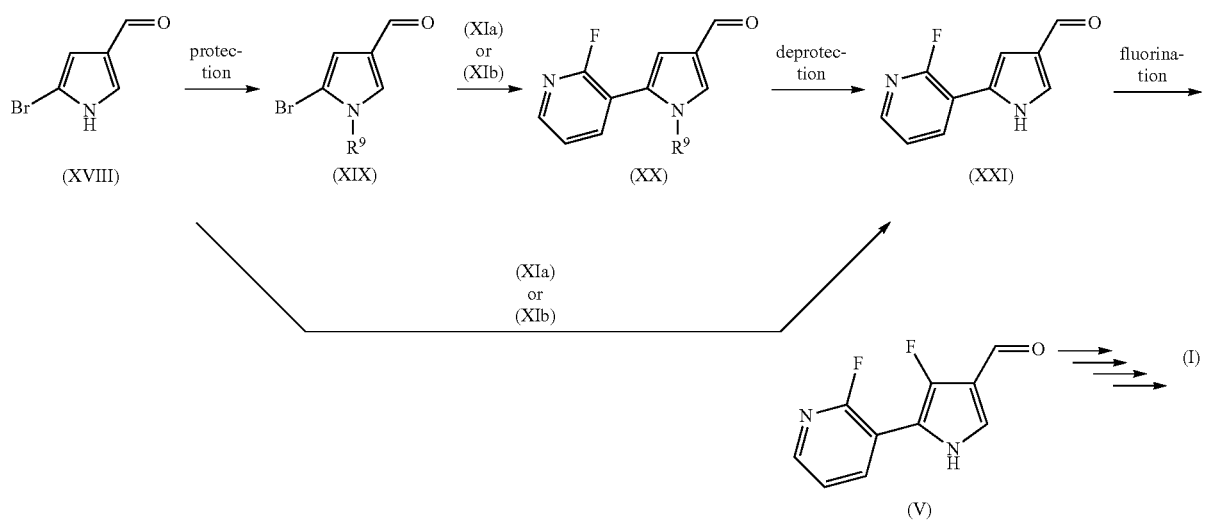

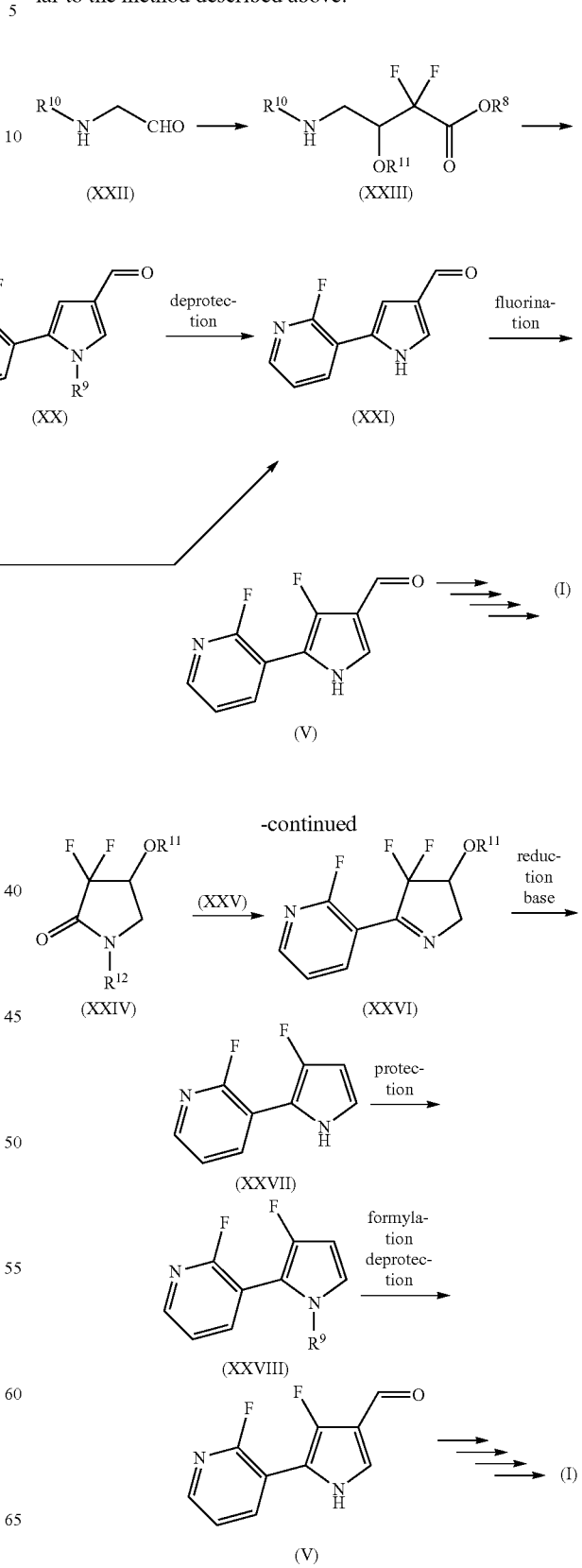

Compound (XVIII) can be produced according to a method known per se, for example, the method described in Journal of Organic Chemistry (J. Org. Chem.), vol. 55, p. 6317 (1990) and the like, or a method analogous thereto.

Compound (XIX) wherein each symbol is as defined above can be produced from compound (XVIII) according to a method similar to the method for producing compound (X) from compound (IX).

Compound (XX) wherein each symbol is as defined above can be produced from compound (XIX) according to a method similar to the method for producing compound (XII) from compound (X).

Compound (XXI) can be produced from compound (XX) according to a method similar to the method for producing compound (II) from compound (XII). Alternatively, compound (XXI) wherein each symbol is as defined above can be produced from compound (XVIII) according to a method similar to the method for producing compound (XII) from compound (X).

Compound (V) can be produced from compound (XXI) according to a method similar to the method for producing Compound (XXII) wherein each symbol is as defined above can be produced according to a method known per se, for example, the method described in Tetrahedron Letters, vol. 40, p. 4905-4908 (1999) and the like, or a method analogous thereto.

Compound (XXIII) wherein $R^{11}$ is a hydroxy-protecting group, and other symbols are as defined above can be produced, for example, according to the method described in Organic Biomolecular Chemistry (Org. Biomol. Chem.), vol. 1, p. 3527-3534 (2003) and the like by reacting compound (XXII) with bromo (or chloro, iodo)difluoroacetic acid ester, and protecting the resulting hydroxy group. The hydroxy-protecting group is not particularly limited as long as the reaction proceeds, and preferable examples include a tosyl group, a mesyl group and the like.

Compound (XXIV) wherein $R^{12}$ is an amide-protecting group, and other symbols are as defined above can be produced by subjecting compound (XXIII) to cyclization reaction via deprotection of an amino group, and protecting the amide group. The conditions of the amino group deprotection and cyclization are not particularly limited as long as the reaction proceeds, and examples thereof include reaction conditions for simultaneous cyclization and deprotection in a hydrogen chloride-ethyl acetate solution and the like. The amide-protecting group is not limited as long as the reaction proceeds, and preferable examples include a tert-butoxycarbonyl group (BOC group) and the like.

Compound (XXVI) wherein each symbol is as defined above can be produced by reacting compound (XXIV) with a compound represented by the formula (XXV) wherein Z is an atom or molecule imparting nucleophilicity such as Li, MgBr and the like.

(XXV)

Compound (XXV) can be produced in a reaction system according to, for example, the method described in Tetrahedron Lett., vol. 21, p. 4137 (1980) or Tetrahedron Lett., vol. 42, p. 8697 (2001), or a method analogous thereto.

The solvent of this reaction is not particularly limited as long as the reaction proceeds, and preferable solvents include hydrocarbons such as n-hexane, toluene and the like, ethers such as tetrahydrofuran, diethyl ether and the like and the like or a mixed solvent thereof and the like. The reaction time varies depending on the substrate and solvent to be used, and is generally 1 min to 48 hr, preferably 10 min to 24 hr.

Compound (XXVII) can be produced according to a method known per se, for example, the method described in Tetrahedron Letters, vol. 36, p. 5119-5122 (1995) and the like, or a method analogous thereto. Alternatively, compound (XXVII) can be produced by reducing compound (XXVI) and reacting the resulting compound with a base. The reducing agent to be used for this reaction is not particularly limited as long as the reaction proceeds, and preferable examples include sodium borohydride and the like.

Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, 1,8-diazabicyclo[5.4.0]undec-7-ene (DBU) and the like, and the like. The amount of the bases to be used is 0.8 to 20 mol, preferably 1 to 10 mol, per 1 mol of compound (XXVI).

This reaction is advantageously carried out using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, acetonitrile and the like or a mixed solvent thereof and the like is preferable. This reaction is advantageous in that it can be performed in the co-presence of crown ethers. Examples of the crown ether include 15-crown-5-ether, 18-crown-6-ether and the like. The amount of the crown ether to be used is 0.01 to 10 mol, preferably 1 to 5 mol, per 1 mol of compound (XXVI). While the reaction time varies depending on the reagents and solvent to be used, it is generally 1 min to 48 hr, preferably 10 min to 8 hr. The reaction temperature is generally −78° C. to 100° C., preferably −10° C. to 70° C.

Compound (XXVIII) wherein each symbol is as defined above can be produced from compound (XXVII) according to a method similar to the method for producing compound (X) from compound (IX).

Compound (V) can be produced from compound (XXVIII), for example, by a typical formylation reaction including treating a reaction product of oxalyl chloride with dimethylformamide, and the like. In addition, compound (V) can be produced by a method including introducing a cyano group and carboxylic acid and converting the resulting compound to aldehyde and the like. In addition, compound (XVI) can also be produced according to the following method, and compound (I) can be produced using a method similar to the method described above.

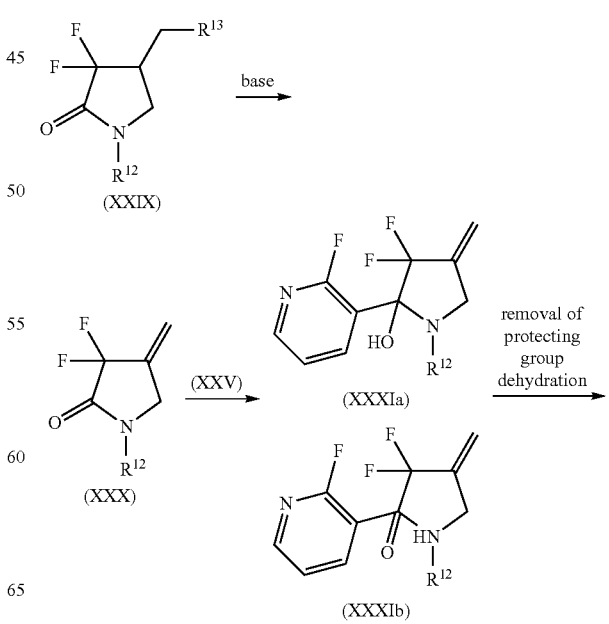

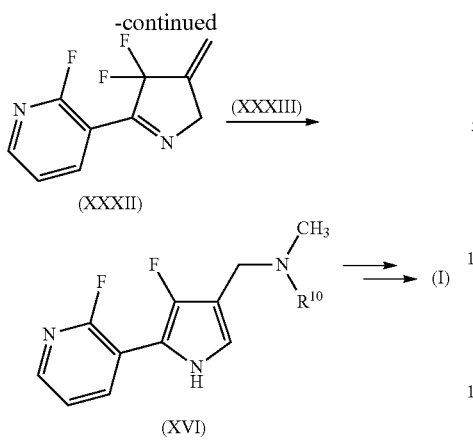

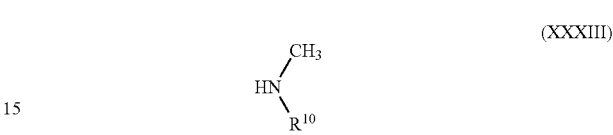

Compound (XXIX) wherein R$^{12}$ is as defined above, and R$^{13}$ is a halogen atom such as a chlorine atom, a bromine atom, an iodine atom and the like can be produced according to a method known per se, for example, the method described in Journal of Organic Chemistry (J. Org. Chem.), vol. 66, p. 315 (2001) and the like, or a method analogous thereto. Examples of the amide-protecting group for R$^{12}$ include, but is not particularly limited to, a tert-butoxycarbonyl group (BOC group), a tosyl group, a benzyl group, an allyl group and the like.

Compound (XXX) wherein each symbol is as defined above can be produced by treating compound (XXIX) with a base. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, 1,8-diazabicyclo[5.4.0]undec-7-ene (DBU), etc. and the like. The amount of the base to be used is 0.8 to 10 mol, preferably 1 to 5 mol, per 1 mol of compound (XXIX).

This reaction is advantageously carried out using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, acetonitrile and the like or a mixed solvent thereof and the like is preferable. While the reaction time varies depending on the reagents and solvent to be used, it is generally 1 min to 48 hr, preferably 10 min to 8 hr. The reaction temperature is generally −78° C. to 100° C., preferably −10° C. to 70° C.

Compound (XXXIa) wherein each symbol is as defined above or compound (XXXIb) wherein each symbols in the formula is as defined above can be produced from compound (XXX) according to a method similar to the method for producing compound (XXVI) from compound (XXIV).

Compound (XXXII) can be produced by subjecting compound (XXXIa) or compound (XXXIb) to deprotection and dehydrating reaction. While the reaction condition is not particularly limited, it varies depending on the kind of the protecting group and the solvent to be used. For example, the deprotection and the dehydrating reaction continuously proceed by treating with an acid such as trifluoroacetic acid and hydrochloric acid.

Compound (XVI) wherein each symbol is as defined above can be produced by treating a compound represented by the formula (XXXIII) wherein each symbol is as defined above with a base such as sodium hydride, n-butyllithium and the like and reacting the resulting compound with compound (XXXII).

The protecting group for R$^{10}$ in this reaction is not particularly limited as long as it is removable, and preferable examples include a benzyl group, a 4-methoxybenzyl group, a 2,4-dimethoxybenzyl group and the like.

While the solvent used for this reaction is not particularly limited as long as the reaction proceeds, hydrocarbons such as n-hexane, toluene and the like, ethers such as tetrahydrofuran, diethyl ether and the like or a mixed solvent thereof and the like are preferable. While the reaction time varies depending on the substrates and solvent to be used, it is generally 1 min to 48 hr, preferably 10 min to 5 hr. The reaction temperature is generally −100° C. to 100° C., preferably −78° C. to 30° C.

Compound (I) can be isolated and purified by a known means such as phase transfer, concentration, solvent extraction, fractionation, liquid conversion, crystallization, recrystallization, chromatography and the like. When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis with gastric acid, and the like. The prodrug of compound (I) includes a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxy group of compound (I) is modified with acyl, alkyl, phosphoric acid or boric acid (e.g., a compound wherein the hydroxy group of compound (I) is modified with acetyl, palmitoyl, propanoyl, pivaloyl, succinyl, fumaryl, alanyl or dimethylaminomethylcarbonyl, etc.); a compound wherein a carboxyl group of compound (I) is modified to ester or amide (e.g., a compound wherein a carboxyl group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from compound (I) by a method known per se. In addition, the prodrug of compound (I) may be a compound, which is converted to compound (I) under the physiological conditions, as described in Pharmaceutical Research and Development, Vol. 7 (Molecule Design), pp. 163-198 (1990), published by Hirokawa Publishing Co.

When compound (I) contains an optical isomer, a stereoisomer, a regioisomer or a rotamer, all of these isomers and a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.).

Compound (I) may be a crystal, and both a single crystal and crystal mixtures are encompassed in compound (I). Crystals can be produced by crystallization according to crystallization methods known per se.

Compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) and a deuterium conversion form wherein $^1$H has been converted to $^2$H(D) are also encompassed in the compound (I).

Compound (I) or a salt thereof or a prodrug thereof of the present invention (hereinafter sometimes to be abbreviated as the compound of the present invention) have a proton pump inhibitory effect and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy exhibition, they are useful as medicaments.

The compound of the present invention is useful for the prophylaxis or treatment of peptic ulcer (e.g., gastric ulcer, duodenal ulcer, anastomotic ulcer, ulcer caused by non-steroidal anti-inflammatory drug, ulcer due to postoperative stress etc.); Zollinger-Ellison syndrome; gastritis; erosive esophagitis; reflux esophagitis such as erosive reflux esophagitis and the like; symptomatic gastroesophageal reflux disease (Symptomatic GERD) such as nonerosive esophageal reflux, esophageal reflux unaccompanied by esophagitis and the like; Barrett's esophagus; functional dyspepsia; gastric cancer (including gastric cancer associated with promoted production of interleukin-1β due to gene polymorphism of interleukin-1); stomach MALT lymphoma; hyperacidity; upper gastrointestinal bleeding caused by peptic ulcer, acute stress ulcer, hemorrhagic gastritis, invasive stress (e.g., stress caused by major surgery requiring post-operative intensive management, or cerebrovascular disorder, head injury, multiple organ failure or extensive burn requiring intensive treatment) and the like; airway disorders; asthma; and the like in mammals (e.g., human, monkey, sheep, bovine, horse, dog, cat, rabbit, rat, mouse etc.), pre-anesthetic administration, eradication or assisting eradication of *Helicobacter pylori* and the like. As used herein, the above-mentioned reflux esophagitis (erosive esophagitis) and symptomatic gastroesophageal reflux disease (symptomatic GERD) are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be safely administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, orally disintegrating film, liquid, injection, suppository, sustained-release preparation, plaster and the like. Particularly, the compound of the present invention is preferably administered as an oral preparation in the form of tablet, granule, capsule and the like.

The pharmacologically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, solubilizing agents, suspending agents, isotonizing agents, buffers and soothing agents for liquid preparations and the like. Ordinary pharmaceutical additives such as preservatives, anti-oxidants, colorants, sweetening agents, souring agents, bubbling agents and flavorings may also be used as necessary. Such "excipients" include, for example, lactose, sucrose, D-mannitol, starch, cornstarch, crystalline cellulose, light anhydrous silicic acid, titanium oxide and the like. Such "lubricants" include, for example, magnesium stearate, sucrose fatty acid esters, polyethylene glycol, talc, stearic acid and the like. Such "binders" include, for example, hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like. Such "disintegrants" include (1) crosspovidone, (2) what is called super-disintegrants such as crosscarmellose sodium (manufactured by FMC-Asahi Chemical Industry Co. Ltd.) and carmellose calcium (manufactured by Gotoku Yakuhin) etc, (3) sodium carboxymethyl starch (e.g., product of Matsutani Chemical), (4) low-substituted hydroxypropyl cellulose (e.g., product of Shin-Etsu Chemical), (5) corn starch, and so forth. Said "crosspovidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by KOLLIDON CL (registered trademark; produced by BASF), POLYPLASDON XL (registered trademark; produced by ISP), POLYPLASDON XL-10 (registered trademark; produced by ISP), POLYPLASDON INF-10 (registered trademark; produced by ISP) and the like. Such "water-soluble polymers" include, for example, ethanol-soluble water-soluble polymers [e.g., cellulose derivatives such as hydroxypropyl cellulose (hereinafter also referred to as HPC) etc, polyvinylpyrrolidone and the like], ethanol-insoluble water-soluble polymers [e.g., cellulose derivatives such as hydroxypropylmethyl cellulose (hereinafter also referred to as HPMC) etc., methyl cellulose, carboxymethyl cellulose sodium and the like, sodium polyacrylate, polyvinyl alcohol, sodium alginate, guar gum and the like] and the like. Such "basic inorganic salts" include, for example, basic inorganic salts of sodium, potassium, magnesium and/or calcium. Preferred are basic inorganic salts of magnesium and/or calcium.

More preferred are basic inorganic salts of magnesium. Such basic inorganic salts of sodium include, for example, sodium carbonate, sodium hydrogen carbonate, disodium hydrogenphosphate and the like. Such basic inorganic salts of potassium include, for example, potassium carbonate, potassium hydrogencarbonate and the like. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}.CO_3.4H_2O$], and aluminum magnesium hydroxide. Preferred are heavy magnesium carbonate, magnesium carbonate, magnesium oxide, magnesium hydroxide and the like. Such basic inorganic salts of calcium include, for example, precipitated calcium carbonate, calcium hydroxide, etc. Such "solvents" include, for example, water for injection, alcohol, propylene glycol, macrogol, sesame oil, corn oil, olive oil and the like. Such "solubilizing agents" include, for example, polyethylene glycol, propylene glycol, D-mannitol, benzyl benzoate, ethanol, trisaminomethane, cholesterol, triethanolamine, sodium carbonate, sodium citrate and the like. Such "suspending agents" include, for example, surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose etc., and the like. Such "isotonizing agents" include, for example, glucose, D-sorbitol, sodium chloride, glycerol, D-mannitol and the like. Such "buffers" include, for example, buffer solutions of phosphates, acetates, carbonates, citrates etc, and the like. Such "soothing agents" include, for example, benzyl alcohol and the like. Such "preservatives" include, for example, p-oxybenzoic acid esters, chlorobutanol, benzyl alcohol, phenethyl alcohol, dehydroacetic acid, sorbic acid and the like. Such "antioxidants" include, for example, sulfites, ascorbic acid, α-tocopherol and the like. Such "colorants" include, for example, food colors such as Food Color Yellow No. 5, Food Color Red No. 2, Food Color Blue No. 2 etc.; food lake colors, red ferric oxide and the like. Such "sweetening agents" include, for example, saccharin sodium, dipotassium glycyrrhizinate, aspartame, stevia, thaumatin and the like. Such "souring agents" include, for example, citric acid (citric anhydride), tartaric acid, malic acid and the like. Such "bubbling agents" include, for example, sodium bicarbonate and the like. Such "flavorings" may be synthetic substances or naturally occurring substances, and include, for example, lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include, for example, a method in which a core containing crystalline cellulose and lactose is coated with the compound of the present invention and, where necessary, a basic inorganic salt, and then further coated with a coating layer containing an water-soluble polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

The above-mentioned "enteric coating layer" includes, for example, a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., EUDRAGIT (registered trademark; produced by Rohm) L30D-55, COLICOAT (registered trademark; produced by BASF) MAE30DP, POLYQUID (registered trademark; produced by San-yo Chemical) PA30 etc.), carboxymethylethyl cellulose, shellac and the like; sustained-release substrates such as methacrylic acid copolymers (e.g., EUDRAGIT (registered trademark) NE30D, EUDRAGIT (registered trademark) RL30D, EUDRAGIT (registered trademark) RS30D, etc.) and the like; water-soluble polymers; plasticizers such as triethyl citrate, polyethylene glycol, acetylated monoglycerides, triacetin, castor oil and the like; and the like, and the like.

The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose (e.g., CEOLAS (registered trademark) KG 801, Avicel (registered trademark) PH 101, AVICEL (registered trademark) PH 102, AVICEL (registered trademark) PH 301, AVICEL (registered trademark) PH 302, AVICEL (registered trademark) RC-591 (crystalline cellulose.carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, colorants, stabilizers, excipients, disintegrants etc. are also used.

The compound of the present invention may be used in combination with 1 to 3 other active ingredients. Such "other active ingredients" include, for example, anti-*Helicobacter pylori* active substances, imidazole compounds, bismuth salts, quinolone compounds, and so forth. Examples of the "anti-*Helicobacter pylori* active substance" include penicillin antibiotic (e.g., amoxicillin, benzylpenicillin, piperacillin, mecillinam, ampicillin, temocillin, bacampicillin, aspoxicillin, sultamicillin, lenampicillin etc.), cephem antibiotic (e.g., cefixime, cefaclor etc.), macrolide antibiotic (e.g., erythromycin, clarithromycin, roxithromycin, rokitamycin, flurithromycin, telithromycin etc.), tetracycline antibiotic (e.g., tetracycline, minocycline, streptomycin etc.), aminoglycoside antibiotic (e.g., gentamicin, amikacin etc.), imipenem and the like. Of these, penicillin antibiotic, macrolide antibiotic and the like are preferable. Such "imidazole compounds" include, for example, metronidazole, miconazole and the like. Such "bismuth salts" include, for example, bismuth acetate, bismuth citrate, bismuth subsalicylate and the like. Such "quinolone compounds" include, for example, ofloxacin, ciploxacin and the like. For eradication of *Helicobacter pylori*, a compound (I) or a salt thereof of the present invention with penicillin antibiotic (e.g., amoxicillin and the like) and erythromycin antibiotic (e.g., clarithromycin and the like) is preferably used.

For the purpose of eradication of *Helicobacter pylori*, while the compound of the present invention has an anti-*H. pylori* action (bacteriostatic action or eradication action) by itself, it can enhance antibacterial action of other antibiotics based on the pH controlling action in the stomach and the like, and also provides an assisting effect such as an eradication effect based on the action of the antibiotics to be used in combination. Such "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

In addition, the compound of the present invention may be used in combination with a prokinetic drug, a drug acting on lower esophageal sphincter (e.g., transientlower esophageal sphincter relaxation suppressant etc.), ClC-2 channel opener (stimulant of intestinal juice secretion), a histamine $H_2$ receptor antagonist, an antacid, a sedative, a stomachic or a non-steroidal anti-inflammatory drug (NSAID). As the "prokinetic drug", for example, domperidone, metoclopramide, mosapride, itopride, tegaserod and the like can be mentioned. As the "a drug acting on lower esophageal sphincter", for example, GABA-B receptor agonists such as baclofen, an optically active form thereof and the like, glutamine receptor antagonists and the like can be mentioned. As the "ClC-2 channel opener (stimulant of intestinal juice secretion)", lubiprostone and the like can be mentioned. As the "histamine $H_2$ receptor antagonist", cimetidine, ranitidine, famotidine, roxatidine, nizatidine, lafutidine and the like can be mentioned. As the "antacid", sodium hydrogen carbonate, aluminum hydroxide and the like can be mentioned. As the "sedatives", diazepam, chlordiazepoxide and the like can be mentioned. As the "stomachic", *gentiana, swertia japonica,* diastase and the like can be mentioned. As the "non-steroidal anti-inflammatory drug", for example, aspirin, indomethacin, ibuprofen, mefenamic acid, diclofenac, etodorac, piroxicam, celecoxib and the like can be mentioned.

A prokinetic drug, a drug acting on lower esophageal sphincter, a ClC-2 channel opener (stimulant of intestinal juice secretion), a histamine $H_2$ receptor antagonist, an antacid, a sedative, a stomachic or a non-steroidal anti-inflammatory drug and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a time-lag manner.

The compound of the present invention may be used in combination with the following drugs.

(i) proton pump inhibitor, for example, omeprazole, esomeprazole, pantoprazole, rabeprazole, tenatoprazole, ilaprazole and lansoprazole;

(ii) oral antacid combination agent, for example, MAALOX, ALUDROX and GAVISCON;

(iii) mucous membrane protector, for example, polaprezinc, ecabe sodium, rebamipide, teprenone, cetraxate, sucralfate, chloropylline-copper and plaunotol;

(iv) antigastric agent, for example, anti-gastrin vaccine, itriglumide and Z-360;

(v) 5-$HT_3$ antagonist, for example, dolasetron, palonosetron, alosetron, azasetron, ramosetron, mitrazapine, granisetron, tropisetron, E-3620, ondansetron and indisetron;

(vi) 5-$HT_4$ agonist, for example, tegaserod, mosapride, cinitapride and oxtriptane;

(vii) laxative agent, for example, TRIFYBA, FYBOGEL, KONSYL, ISOGEL, REGULAN, CELEVAC and NORMACOL;

(viii) $GABA_B$ agonist, for example, baclofen and AZD-3355;

(ix) $GABA_B$ antagonist, for example, GAS-360 and SGS-742;

(x) calcium channel blocker, for example, aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonist, for example, metoclopramide, domperidone and levosulpiride;

(xii) tachykinin (NK) antagonist, particularly, NK-3, NK-2 and NK-1 antagonist, for example, nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6,13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and (2S,3S)-3-[[2-methoxy-5-(trifluoromethoxy)phenyl]methylamino]-2-phenyl-piperidine;

(xiii) nitric monoxide synthase inhibitor, for example, GW-274150, tilarginine, P54, guanidioethyldisulfide and nitroflurbiprofen;

(xiv) vanilloid receptor 1 antagonist, for example, AMG-517 and GW-705498;

(xv) ghrelin agonist, for example, capromorelin and TZP-101;

(xvi) ACNE inhibitor, for example, Z-338 and KW-5092.

The above-mentioned drugs (i)-(xvi) and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a time-lag manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK, Fuji Silysia Chemical Ltd. CHROMATOREX (trade name) NH (described as basic silica gel column chromatography) or PURIF-PACK manufactured by MORITEX (described as silica gel column chromatography or basic silica gel column chromatography). The melting point was measured using Yanagimoto trace melting point measurement apparatus or Buechi trace melting point measurement apparatus (B-545), and shown without amendment. For $^1$H-NMR spectrum, tetramethylsilane was used as the internal standard, and Varian Gemini-200 (200 MHz), Mercury-300 (300 MHz) spectrometer, Bruker AVANCE AV300 (300 MHz) and JNM-AL400

(400 MHz) nuclear magnetic resonance apparatuses JEOL DATUM (JEOL DATUM LTD.) were used for the measurement. The following abbreviations are used for showing the measurement results. s: singlet, d: doublet, dd: double doublet, ddd: triple doublet, dt: double triplet, t: triplet, q: quartet, dq: double quartet, m: multiplet, br: broad, brs: broad singlet, J: coupling constant, Hz: Hertz.

Reference Example 1 tert-Butyl (2-oxoethyl)carbamate

To a mixed solution of tert-butyl (2-hydroxyethyl)carbamate (10.0 g) in dimethyl sulfoxide (50 mL) and triethylamine (12.3 g) was added sulfur trioxide pyridine complex (15.0 g) under ice-cooling, and the mixture was stirred for 1 hr. The reaction mixture was further stirred at room temperature for 3 hr, 1 mol/L hydrochloric acid was added, and the mixture was extracted with ethyl acetate. The separated aqueous layer was extracted again with ethyl acetate. The combined organic layers were washed with saturated brine, dried over magnesium sulfate and concentrated under reduced pressure. The residue was purified by silica gel column chromatography (eluent:hexane-ethyl acetate=17:3→13:7) to give the title compound as a pale-yellow oil (yield 6.50 g, 66%).
$^1$H-NMR (CDCl$_3$) δ:1.46(9H,s), 4.08(2H,d,J=4.5 Hz), 5.19(1H,brs), 9.66(1H,s).

Reference Example 2

Ethyl 4-[(tert-butoxycarbonyl)amino]-2,2-difluoro-3-{[(4-methylphenyl)sulfonyl]oxy}butanoate Zinc powder (23.0 g) was washed with 0.1 mol/L hydrochloric acid, ethanol and diethyl ether, and dried under reduced pressure. Under an argon atmosphere, to a suspension of washed zinc powder in tetrahydrofuran (300 mL) was added a solution of tert-butyl (2-oxoethyl)carbamate (35.0 g) in tetrahydrofuran (50 mL), ethyl bromodifluoroacetate (75.9 g) was gradually added dropwise under ice-cooling, and the mixture was stirred for 15 min. 1 mol/L Hydrochloric acid was added to the reaction mixture, and the mixture was extracted with ethyl acetate. The separated aqueous layer was extracted again with ethyl acetate. Combined organic layers were washed with saturated aqueous sodium hydrogen carbonate solution, water and saturated brine, dried over anhydrous magnesium sulfate and concentrated under reduced pressure. The residue was dissolved in a mixed solution of tetrahydrofuran (30 mL) and pyridine (40 mL), triethylamine (19 mL), 4-dimethylaminopyridine (3.35 g) and 4-methylbenzenesulfonyl chloride (39.2 g) were added at room temperature, and the mixture was stirred at for 2 hr. The reaction mixture was concentrated under reduced pressure, and the residue was dissolved in ethyl acetate, and washed twice with 1 mol/L hydrochloric acid. The separated aqueous layer was extracted again with ethyl acetate. Combined organic layers were washed with saturated aqueous sodium hydrogen carbonate solution, water and saturated brine, dried over anhydrous magnesium sulfate, and concentrated under reduced pressure. The residue was purified by silica gel column chromatography (eluent:hexane-ethyl acetate=4:1) to give the title compound as a pale-yellow oil (yield 44.8 g, 46%).
$^1$H-NMR (CDCl$_3$)δ: 1.33(3H,t,J=7.2 Hz), 1.46(9H,s), 2.46 (3H,s), 3.26-3.43(1H,m), 3.71(1H,brs), 4.28(2H,q,J=7.1 Hz), 4.77(1H,brs), 5.08-5.24(1H,m), 7.35(2H,d,J=8.1 Hz), 7.80 (2H,d,J=8.1 Hz).

Reference Example 3 tert-Butyl 3,3-difluoro-4-{[(4-methylphenyl)sulfonyl]oxy}-2-oxopyrrolidine-1-carboxylate To a solution of ethyl 4-[(tert-butoxycarbonyl)amino]-2,2-difluoro-3-{[(4-methylphenyl)sulfonyl]oxy}butanoate (44.8 g) in ethyl acetate (50 mL) was added 4 mol/L hydrogen chloride-ethyl acetate solution (100 mL), and the mixture was stirred for 3 hr. The reaction mixture was concentrated under reduced pressure, and the residue was azeotropically distilled twice with toluene. The obtained mixture was dissolved in acetonitrile (20 mL), triethylamine (15.6 g) was added, and the mixture was stirred for 3 hr. Di-tert-butyl bicarbonate (33.6 g) and 4-dimethylaminopyridine (3.76 g) were added at room temperature and the mixture was stirred for 1 hr. The reaction mixture was concentrated under reduced pressure, and the residue was dissolved in ethyl acetate, and washed with 1 mol/L hydrochloric acid. The separated aqueous layer was extracted again with ethyl acetate. Combined organic layers were washed with saturated aqueous sodium hydrogen carbonate solution, water and saturated brine, dried over anhydrous magnesium sulfate and concentrated under reduced pressure. The residue was purified by silica gel column chromatography (eluent:hexane-ethyl acetate=2:1) to give the title compound as a pale-yellow oil (yield 32.0 g, 80%).
$^1$H-NMR (CDCl$_3$)δ: 1.55(9H,s), 2.48(3H,s), 3.81-3.91 (1H,m), 4.09-4.18(1H,m), 4.94-5.06(1H,m), 7.40(2H,d, J=8.1 Hz), 7.83(2H,d,J=8.1 Hz).

Reference Example 4

4,4-Difluoro-5-(2-fluoropyridin-3-yl)-3,4-dihydro-2H-pyrrol-3-yl 4-methylbenzenesulfonate To a solution of diisopropylamine (8.76 g) in tetrahydrofuran (230 mL) was added 1.6 mol/L n-butyllithium hexane solution (51 mL) at −78° C., and the mixture was stirred for 1 hr. 2-Fluoropyridine (11.2 g) was added dropwise thereto, and the mixture was stirred for 2 hr. To the resultant pale-yellow suspension was slowly added dropwise a solution of tert-butyl 3,3-difluoro-4-{[(4-methylphenyl)sulfonyl]oxy}-2-oxopyrrolidine-1-carboxylate (22.6 g) in tetrahydrofuran (50 mL), and the mixture was stirred for 1 hr. Water was added to the reaction mixture, and the mixture was heated to room temperature and concentrated under reduced pressure. The residue was diluted with ethyl acetate, and washed with water. The separated aqueous layer was extracted again with ethyl acetate. Combined organic layers were washed with saturated brine, dried over anhydrous magnesium sulfate and concentrated under reduced pressure. The obtained mixture was dissolved in dichloromethane (30 mL), trifluoroacetic acid (100 mL) was added dropwise under ice-cooling, and the mixture was stirred for 4 hr while allowing the mixture to warm to room temperature. The reaction mixture was concentrated under reduced pressure, diluted with ethyl acetate, and a saturated aqueous sodium hydrogen carbonate solution was added until the mixture became neutral. The separated aqueous layer was extracted again with ethyl acetate. Combined organic layers were washed with saturated brine, dried over magnesium sulfate, and concentrated under reduced pressure. The residue was purified by silica gel column chromatography (eluent:hexane-ethyl acetate=9:1→3:1) to give the title compound as a colorless solid (yield 10.9 g, 51%).

¹H-NMR (CDCl₃)δ: 2.48(3H,s), 4.17-4.28(1H,m), 4.42-4.54(1H,m), 5.06-5.13(1H,m), 7.31(1H,ddd,J=7.6,4.9,1.9 Hz), 7.39(2H,d,J=7.9 Hz), 7.85(2H,d,J=8.3 Hz), 8.22-8.31 (1H,m), 8.34-8.39(1H,m).

Reference Example 5

2-Fluoro-3-(3-fluoro-1H-pyrrol-2-yl)pyridine

To a solution of 4,4-difluoro-5-(2-fluoropyridin-3-yl)-3,4-dihydro-2H-pyrrol-3-yl 4-methylbenzenesulfonate (18.0 g) in tetrahydrofuran (180 mL) was added sodium borohydride (3.68 g) under ice-cooling, methanol (90 mL) was further added, and the mixture was stirred for 3 hr. The reaction mixture was concentrated under reduced pressure, and the residue was diluted with ethyl acetate and washed with water. The separated aqueous layer was extracted again with ethyl acetate. Combined organic layers were washed with saturated brine, dried over anhydrous magnesium sulfate and concentrated under reduced pressure to give 4,4-difluoro-5-(2-fluoropyridin-3-yl)pyrrolidin-3-yl 4-methylbenzenesulfonate. To a suspension of sodium hydride (9.74 g) in tetrahydrofuran (100 mL) was added dropwise a solution of 4,4-difluoro-5-(2-fluoropyridin-3-yl)pyrrolidin-3-yl 4-methylbenzenesulfonate in tetrahydrofuran (100 mL) under ice-cooling, 15-crown-5 (32.2 g) was added, and the mixture was stirred for 3 hr. Saturated aqueous ammonium chloride solution was added to the reaction mixture and concentrated under reduced pressure. The residue was diluted with ethyl acetate, and washed with 1 mol/L hydrochloric acid. The separated aqueous layer was extracted again with ethyl acetate. Combined organic layers were washed with saturated aqueous sodium hydrogen carbonate solution, water and saturated brine, dried over anhydrous magnesium sulfate and concentrated under reduced pressure. The residue was purified by silica gel column chromatography (eluent:hexane-ethyl acetate=9:1→3:1) to give the title compound as a colorless solid (yield 6.35 g, 72%).

¹H-NMR (CDCl₃)δ: 6.10(1H,t,J=2.9 Hz), 6.69(1H,dt, J=4.6,3.4 Hz), 7.20-7.30(1H,m), 8.00(1H,dt,J=4.7,1.7 Hz), 8.25(1H,ddd,J=10.3,7.8,1.9 Hz), 8.69(1H,brs).

Reference Example 6

2-Fluoro-3-{3-fluoro-1-[tris(1-methylethyl)silyl]-1H-pyrrol-2-yl}pyridine

To a suspension of sodium hydride (3.32 g) in tetrahydrofuran (70 mL) was added dropwise a solution of 2-fluoro-3-(3-fluoro-1H-pyrrol-2-yl)pyridine (5.98 g) in tetrahydrofuran (30 mL) under ice-cooling and the mixture was stirred for 30 min. 15-Crown-5 (18.3 g) and tris(1-methylethyl)silyl trifluoromethanesulfonate (25.4 g) were added, and the mixture was stirred for 1 hr. The solvent was evaporated to a half volume under reduced pressure, water was added, and the mixture was extracted with ethyl acetate. The separated aqueous layer was extracted again with ethyl acetate. Combined organic layers were washed with saturated brine, dried over anhydrous magnesium sulfate and concentrated under reduced pressure.

The residue was purified by basic silica gel column chromatography (eluent:hexane→hexane-ethyl acetate=19:1) to give the title compound as a pale-yellow oil (yield 10.9 g, 98%).

¹H-NMR (CDCl₃)δ: 1.04(18H,d,J=7.0 Hz), 1.09-1.19(3H, m), 6.17(1H,dd,J=3.2,1.5 Hz), 6.70(1H,dd,J=4.8,3.3 Hz), 7.21(1H,ddd,J=7.3,4.9,1.7 Hz), 7.78(1H,ddd,J=9.3,7.3,2.1 Hz).

Reference Example 7

4-Fluoro-5-(2-fluoropyridin-3-yl)-1H-pyrrole-3-carbaldehyde

To a solution of N,N-dimethylformamide (717 mg) in dichloromethane (20 mL) was added oxalyl chloride (1.13 g) under ice-cooling under an argon atmosphere, and the mixture was stirred for 10 min. To the obtained suspension was added a solution of 2-fluoro-3-{3-fluoro-1-[tris(1-methylethyl)silyl]-1H-pyrrol-2-yl}pyridine (1.50 g) in dichloromethane (5 mL) and the mixture was stirred under refluxing conditions for 10 hr. The reaction mixture was cooled under ice-cooling, 1 mol/L aqueous sodium hydroxide solution (30 mL) was added and the mixture was stirred for 15 min. The solvent was evaporated to a half volume under reduced pressure and the residue was partitioned by adding ethyl acetate. The separated aqueous layer was extracted again with ethyl acetate. Combined organic layers were washed with saturated brine, dried over anhydrous sodium sulfate and concentrated under reduced pressure. The residual solid was washed with diisopropyl ether (30 mL) and filtered by suction to give the title compound as a colorless solid (yield 726 mg, 78%).

¹H-NMR (CDCl₃)δ: 7.29-7.40(2H,m), 8.11(1H,dt,J=4.8, 1.6 Hz), 8.29(1H,ddd,J=10.0,7.9,1.9 Hz), 9.22(1H,brs), 9.90 (1H,s).

Reference Example 8 tert-Butyl {[4-fluoro-5-(2-fluoropyridin-3-yl)-1H-pyrrol-3-yl]methyl}methylcarbamate To a solution of 4-fluoro-5-(2-fluoropyridin-3-yl)-1H-pyrrole-3-carbaldehyde (261 mg) in tetrahydrofuran (1 mL)-methanol (2 mL) was added 40% methylamine methanol solution (4 mL) at room temperature, and the mixture was stirred for 20 min. Sodium borohydride (142 mg) was added to the reaction mixture and the mixture was stirred for 1 hr. The reaction mixture was concentrated under reduced pressure, water (4 mL) and ethyl acetate (4 mL) were added. Di-tert-butyl bicarbonate (410 mg) was added to the obtained mixture at room temperature, and the mixture was stirred for 1 hr. The reaction mixture was separated between ethyl acetate and an aqueous layer, and the separated aqueous layer was extracted again with ethyl acetate. Combined organic layers were washed with saturated brine, dried over anhydrous sodium sulfate and concentrated under reduced pressure. The residue was purified by silica gel column chromatography (eluent:hexane-ethyl acetate=9:1→3:1) to give the title compound as a colorless solid (yield 347 mg, 86%).

¹H-NMR (CDCl₃)δ: 1.49(9H,s), 2.88(3H,s), 4.31(2H,s), 6.46-6.94(1H,m), 7.15-7.32(1H,m), 8.00(1H,dt,J=4.7,1.7 Hz), 8.23(1H,ddd,J=10.2,7.9,1.9 Hz), 8.66(1H,brs).

Reference Example 9

2-(Benzylsulfanyl)-3-methylpyridine

To a suspension of sodium hydride (60% in oil, 1.44 g) in tetrahydrofuran (45 mL) was added dropwise phenylmethanethiol (465 mg) at room temperature and the mixture was stirred for 15 min. 2-Bromo-3-methylpyridine (2.0 g)

was added to the reaction mixture, and the mixture was stirred at 60° C. for 1.5 hr. The reaction mixture was diluted with water, and concentrated under reduced pressure. The residual aqueous layer was extracted twice with ethyl acetate. Combined organic layers were washed with saturated brine, dried over anhydrous magnesium sulfate and concentrated under reduced pressure. The residue was purified by silica gel column chromatography (eluent:hexane→hexane-ethyl acetate=97:3) to give the title compound as a gray oil (yield 1.79 g, 72%).

$^1$H-NMR (CDCl$_3$)δ: 2.23(3H,s), 4.49(2H,s), 6.93(1H,dd, J=7.6,4.9 Hz), 7.19-7.35(5H,m), 7.39-7.48(1H,m), 8.32(1H, dd,J=4.9,1.1 Hz).

Reference Example 10

3-Methylpyridine-2-sulfonyl chloride

To a solution of 2-(benzylsulfanyl)-3-methylpyridine (1.79 g) in acetic acid (16 mL)-water (8 mL) was added N-chlorosuccinimide (3.33 g) at room temperature, and the mixture was stirred for 2 hr. The reaction mixture was concentrated under reduced pressure, saturated aqueous sodium hydrogen carbonate solution was added and the mixture was extracted twice with ethyl acetate. Combined organic layers were washed with saturated brine, dried over anhydrous magnesium sulfate and concentrated under reduced pressure. The residue was purified by silica gel column chromatography (eluent:hexane-ethyl acetate=9:1→3:2) to give the title compound as a crude pale-yellow oil (yield 153 mg).

$^1$H-NMR (CDCl$_3$)δ: 2.78(3H,s), 7.57(1H,dd,J=7.9,4.5 Hz), 7.82(1H,ddd,J=7.7,1.5,0.8 Hz), 8.61(1H,dd,J=4.5,1.1 Hz).

Reference Example 11 tert-Butyl ({4-fluoro-5-(2-fluoropyridin-3-yl)-1-[(3-methylpyridin-2-yl)sulfonyl]-1H-pyrrol-3-yl}methyl)methylcarbamate To a suspension of sodium hydride (60% in oil, 20 mg) in tetrahydrofuran (2 mL) was added a solution of tert-butyl {[4-fluoro-5-(2-fluoropyridin-3-yl)-1H-pyrrol-3-yl]methyl}methylcarbamate (161 mg), 15-crown-5 (110 mg), crude 3-methylpyridine-2-sulfonyl chloride (153 mg) in tetrahydrofuran (1.5 mL) at room temperature, and the mixture was stirred at room temperature for 72 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=9:1→11:9) to give the title compound as a colorless oil (yield 113 mg, 47%).

$^1$H-NMR (CDCl$_3$)δ: 1.47(9H,s), 2.43(3H,s), 2.90(3H,s), 4.32(2H,brs), 7.20(1H,ddd,J=7.4,5.0,1.7 Hz), 7.29(1H,d, J=5.7 Hz), 7.36(1H,dd,J=7.8,4.6 Hz), 7.61(1H,dd,J=7.8,0.8 Hz), 7.76-7.85(1H,m), 8.19(1H,ddd,J=4.9,2.0,1.0 Hz), 8.29 (1H,dd,J=4.5,0.9 Hz).

Reference Example 12

2-(Benzylsulfanyl)-4-methylpyridine

To a suspension of sodium hydride (60% in oil, 512 mg) in tetrahydrofuran (45 mL) was added dropwise phenylmethanethiol (1.52 g) at room temperature, 2-bromo-4-methylpyridine (2.0 g) was added, and the mixture was stirred at 60° C. for 72 hr. The reaction mixture was diluted with water and extracted twice with ethyl acetate. Combined organic layers were washed with saturated brine, dried over anhydrous magnesium sulfate and concentrated under reduced pressure. The residue was purified by silica gel column chromatography (eluent:hexane→hexane-ethyl acetate=24:1) to give the title compound as a brown oil (yield 1.40 g, 56%).

$^1$H-NMR (CDCl$_3$)δ: 2.26(3H,s), 4.43(2H,s), 6.82(1H,d, J=5.1 Hz), 6.99(1H,s), 7.17-7.32(3H,m), 7.35-7.44(2H,m), 8.31(1H,d,J=5.1 Hz).

Reference Example 13

4-Methylpyridine-2-sulfonyl fluoride

To a solution of 2-(benzylsulfanyl)-4-methylpyridine (1.40 g) in acetic acid (10 mL)-water (5 mL) was added N-chlorosuccinimide (3.48 g) under ice-cooling, and the mixture was gradually warmed to room temperature and stirred for 4 hr. Potassium fluoride (379 mg) was added at room temperature and the mixture was stirred for 18 hr. The reaction mixture was concentrated under reduced pressure, diluted with ethyl acetate and washed with saturated aqueous sodium hydrogen carbonate solution. The separated aqueous layer was extracted with ethyl acetate. Combined organic layers were washed with saturated brine, dried over anhydrous magnesium sulfate and concentrated under reduced pressure. The residue was purified by silica gel column chromatography (eluent:hexane-ethyl acetate=4:1→1:1) to give the title compound as a crude pale-yellow oil (yield 343 mg, 30%).

$^1$H-NMR (CDCl$_3$)δ: 2.54(3H,s), 7.50(1H,dt,J=4.9,0.7 Hz), 7.95(1H,d,J=0.8 Hz), 8.69(1H,d,J=4.9 Hz).

Reference Example 14 tert-Butyl ({4-fluoro-5-(2-fluoropyridin-3-yl)-1-[(4-methylpyridin-2-yl)sulfonyl]-1H-pyrrol-3-yl}methyl)methylcarbamate To a suspension (3 mL) of sodium hydride (60% in oil, 60 mg) in tetrahydrofuran were added tert-butyl {[4-fluoro-5-(2-fluoropyridin-3-yl)-1H-pyrrol-3-yl]methyl}methylcarbamate (323 mg), 15-crown-5 (330 mg) and 4-methylpyridine-2-sulfonyl fluoride (343 mg) at room temperature, and the mixture was stirred at room temperature for 41 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=4:1→1:1) to give the title compound as a pale-yellow oil (yield 333 mg, 70%).

$^1$H-NMR (CDCl$_3$)δ: 1.47(9H,s), 2.38(3H,s), 2.86(3H,s), 4.27(2H,brs), 7.27-7.34(3H,m), 7.36(1H,s), 7.87(1H,ddd, J=9.2,7.5,1.9 Hz), 8.26(1H,d,J=3.8 Hz), 8.45(1H,d,J=4.9 Hz).

Reference Example 15

2-(Benzylsulfanyl)-5-fluoropyridine

To a suspension of sodium hydride (60% in oil, 440 mg) in tetrahydrofuran (40 mL) was added dropwise phenylmethanethiol (1.37 g) at room temperature, 2-bromo-5-fluoropyridine (1.76 g) was added to the reaction mixture, and the mixture was stirred at 60° C. for 5 hr. The reaction mixture was diluted with water and concentrated under reduced pressure. The residual aqueous layer was extracted twice with ethyl acetate. Combined organic layers were washed with saturated brine, dried over anhydrous magnesium sulfate and concentrated under reduced pressure. The residue was purified by silica gel column chromatography (eluent: hexane→hexane-ethyl acetate=97:3) to give the title compound as a crude brown oil (yield 244 mg).

Reference Example 16

5-Fluoropyridine-2-sulfonyl fluoride

To a solution of crude 2-(benzylsulfanyl)-5-fluoropyridine (244 mg) in acetic acid (3 mL)-water (1.5 mL) was added N-chlorosuccinimide (594 mg) under ice-cooling, and the mixture was gradually warmed to room temperature and stirred for 2 hr. Potassium fluoride (65 mg) was added at room temperature and the mixture was stirred for 1 hr. The reaction mixture was concentrated under reduced pressure, diluted with water and the mixture was extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=9:1→3:1) to give the title compound as a crude colorless solid (yield 69 mg, 35%).
$^1$H-NMR (CDCl$_3$)δ: 7.75(1H,ddd,J=8.7,7.4,2.7 Hz), 8.20 (1H,dd,J=8.8,4.1 Hz), 8.66(1H,d,J=2.8 Hz).

Reference Example 17 tert-Butyl ({4-fluoro-5-(2-fluoropyridin-3-yl)-1-[(5-fluoropyridin-2-yl)sulfonyl]-1H-pyrrol-3-yl}methyl)methylcarbamate To a suspension of sodium hydride (60% in oil, 40 mg) in tetrahydrofuran (2.5 mL) were added tert-butyl {[4-fluoro-5-(2-fluoropyridin-3-yl)-1H-pyrrol-3-yl]methyl}methylcarbamate (162 mg), 15-crown-5 (220 mg) and 5-fluoropyridine-2-sulfonyl fluoride (120 mg) at room temperature, and the mixture was stirred at room temperature for 28 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=9:1→7:3) to give the title compound as a pale-yellow oil (yield 69 mg, 29%).
$^1$H-NMR (CDCl$_3$)δ: 1.48(9H,s), 2.88(3H,s), 4.27(2H,brs), 7.24-7.34(2H,m), 7.52(1H,ddd,J=8.7,7.5,2.8 Hz), 7.68(1H, dd,J=8.7,4.1 Hz), 7.85(1H,ddd,J=9.2,7.4,2.0 Hz), 8.27(1H, ddd,J=4.8,1.8,0.9 Hz), 8.45(1H,d,J=2.6 Hz).

Reference Example 18

2-(Benzylsulfanyl)-4-methoxypyridine

To a solution of 2-chloro-4-methoxypyridine (786 mg) in toluene (10 mL) were added phenylmethanethiol (683 mg), N,N-diisopropylethylamine (1.56 g), tris(dibenzylideneacetone)dipalladium(0) (202 mg) and 4,5-bis(diphenylphosphino)-9,9-dimethylxanthene (256 mg), and the mixture was stirred at 80° C. for 26 hr under an argon atmosphere. The reaction mixture was filtered through silica gel and the filtrate was concentrated under reduced pressure. The residue was purified by silica gel column chromatography (eluent: hexane→hexane-ethyl acetate=19:1) to give the title compound as an orange oil (yield 454 mg, 38%).
$^1$H-NMR (CDCl$_3$)δ: 3.79(3H,s), 4.43(2H,s), 6.57(1H,dd, J=5.9,2.5 Hz), 6.68(1H,d,J=2.3 Hz), 7.19-7.34(3H,m), 7.36-7.44(2H,m), 8.27(1H,d,J=5.7 Hz).

Reference Example 19 tert-Butyl ({4-fluoro-5-(2-fluoropyridin-3-yl)-1-[(4-methoxypyridin-2-yl)sulfonyl]-1H-pyrrol-3-yl}methyl)methylcarbamate To a solution of 2-(benzylsulfanyl)-4-methoxypyridine (453 mg) in acetic acid (4 mL)-water (2 mL) was added N-chlorosuccinimide (1.10 g) under ice-cooling, gradually warmed to room temperature and the mixture was stirred for 5 hr. The reaction mixture was concentrated under reduced pressure, diluted with water and extracted twice with ethyl acetate. Combined organic layers were washed with saturated brine, dried over anhydrous magnesium sulfate and concentrated under reduced pressure. The residue was purified by silica gel column chromatography (eluent:hexane-ethyl acetate=3:1→1:1) to give crude 4-methoxypyridine-2-sulfonyl chloride as a pale-yellow oil. Then, to a suspension of sodium hydride (60% in oil, 30 mg) in tetrahydrofuran (2.5 mL) were added tert-butyl {[4-fluoro-5-(2-fluoropyridin-3-yl)-1H-pyrrol-3-yl]methyl}methylcarbamate (162 mg), 15-crown-5 (165 mg) and a solution of crude 4-methoxypyridine-2-sulfonyl chloride obtained above in tetrahydrofuran (2 mL) at room temperature, and the mixture was stirred for 18 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=17:3→1:1) to give the title compound as a colorless oil (yield 96 mg, yield of 2 steps 9%).
$^1$H-NMR (CDCl$_3$)δ: 1.47(9H,s), 2.87(3H,s), 3.84(3H,s), 4.27(2H,brs), 6.94(1H,dd,J=5.6,2.4 Hz), 7.07(1H,d,J=2.4 Hz), 7.28(1H,dd,J=5.3,2.1 Hz), 7.31(1H,d,J=5.7 Hz), 7.87 (1H,ddd,J=9.2,7.5,1.8 Hz), 8.26(1H,d,J=4.7 Hz), 8.39(1H,d, J=5.7 Hz).

Reference Example 20

3-(Benzylsulfanyl)-5-fluoropyridine

To a solution of 3-bromo-5-fluoropyridine (522 mg) in toluene (5 mL) were added phenylmethanethiol (370 mg), N,N-diisopropylethylamine (831 mg), tris(dibenzylideneacetone)dipalladium(0) (108 mg) and 4,5-bis(diphenylphosphino)-9,9-dimethylxanthene (138 mg), and the mixture was stirred under an argon atmosphere at 80° C. for 2 hr. The reaction mixture was diluted with water and extracted with ethyl acetate. The organic layer was washed with saturated brine, dried over anhydrous magnesium sulfate, and filtered through silica gel. The filtrate was concentrated under reduced pressure. The residue was purified by silica gel column chromatography (eluent:hexane→hexane-ethyl acetate=10:1) to give the title compound as an orange oil (yield 587 mg, 90%).

¹H-NMR (CDCl₃)δ: 4.13(2H,s), 7.23-7.33(6H,m), 8.25-8.26(1H,m), 8.30-8.31(1H,m).

Reference Example 21

5-Fluoropyridine-3-sulfonyl chloride

To a solution of 3-(benzylsulfanyl)-5-fluoropyridine (573 mg) in acetic acid (7.5 mL)-water (2.5 mL) was added N-chlorosuccinimide (1.40 g) at room temperature and the mixture was stirred for 1.5 hr.

The reaction mixture was concentrated under reduced pressure, diluted with water and extracted twice with ethyl acetate. Combined organic layers were washed with saturated brine, dried over anhydrous magnesium sulfate and concentrated under reduced pressure. The residue was azeotropically distilled with toluene and purified by silica gel column chromatography (eluent:hexane-ethyl acetate=9:1→7:3) to give the title compound as a colorless oil (yield 376 mg, 74%).

¹H-NMR (CDCl₃)δ: 8.04(1H,ddd,J=7.0,2.7,2.0 Hz), 8.85 (1H,d,J=2.6 Hz), 9.10(1H,dd,J=1.1,0.8 Hz).

Reference Example 22 tert-Butyl ({4-fluoro-5-(2-fluoropyridin-3-yl)-1-[(5-fluoropyridin-3-yl)sulfonyl]-1H-pyrrol-3-yl}methyl)methylcarbamate To a suspension of sodium hydride (60% in oil, 20 mg) in tetrahydrofuran (2 mL) were added tert-butyl {[4-fluoro-5-(2-fluoropyridin-3-yl)-1H-pyrrol-3-yl]methyl}methylcarbamate (162 mg), 15-crown-5 (132 mg) and a solution of 5-fluoropyridine-3-sulfonyl chloride (127 mg) in tetrahydrofuran (1 mL) at room temperature, and the mixture was stirred for 1 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by basic silica gel column chromatography (eluent:hexane-ethyl acetate=9:1→7:3) to give the title compound as a colorless oil (yield 224 mg, 93%).

¹H-NMR (CDCl₃)δ: 1.48(9H,s), 2.88(3H,s), 4.27(2H,s), 7.28-7.36(2H,m), 7.38(1H,d,J=7.2 Hz), 7.73-7.86(1H,m), 8.34(1H,d,J=4.2 Hz), 8.46(1H,s), 8.69(1H,d,J=2.7 Hz).

Reference Example 23

3-(Benzylsulfanyl)-4-methylpyridine

To a solution of 3-bromo-4-methylpyridine (1.0 g) in toluene (12 mL) were added phenylmethanethiol (794 mg), N,N-diisopropylethylamine (1.65 g), tris(dibenzylideneacetone)dipalladium(0) (213 mg) and 4,5-bis(diphenylphosphino)-9,9-dimethylxanthene (269 mg), and the mixture was stirred under an argon atmosphere at 80° C. for 1.5 hr. The reaction mixture was filtered through silica gel, and the filtrate was concentrated under reduced pressure. The residue was purified by silica gel column chromatography (eluent:hexane-ethyl acetate=19:1→3:1→1:1) to give the title compound as a yellow oil (yield 740 mg, 59%).

¹H-NMR (CDCl₃)δ: 2.27(3H,s), 4.07(2H,s), 7.06(1H,d, J=4.9 Hz), 7.14-7.35(5H,m), 8.30(1H,d,J=5.3 Hz), 8.45 (1H,s).

Reference Example 24

4-Methylpyridine-3-sulfonyl chloride

To a solution of 3-(benzylsulfanyl)-4-methylpyridine (740 mg) in acetic acid (9 mL)-water (3 mL) was added N-chlorosuccinimide (1.84 g) at room temperature, and the mixture was stirred for 2 hr. The reaction mixture was concentrated under reduced pressure, diluted with water and extracted twice with ethyl acetate. Combined organic layers were washed with saturated aqueous sodium hydrogen carbonate solution and saturated brine, dried over anhydrous magnesium sulfate and concentrated under reduced pressure. The residue was azeotropically distilled with toluene and purified by silica gel column chromatography (eluent:hexane-ethyl acetate=9:1→3:1) to give the title compound as a crude colorless oil (yield 676 mg).

¹H-NMR (CDCl₃)δ: 2.82(3H,s), 7.34-7.44(1H,m), 8.77 (1H,d,J=4.9 Hz), 9.19(1H,s).

Reference Example 25 tert-Butyl ({4-fluoro-5-(2-fluoropyridin-3-yl)-1-[(4-methylpyridin-3-yl)sulfonyl]-1H-pyrrol-3-yl}methyl)methylcarbamate To a suspension of sodium hydride (60% in oil, 24 mg) in tetrahydrofuran (2 mL) were added tert-butyl {[4-fluoro-5-(2-fluoropyridin-3-yl)-1H-pyrrol-3-yl]methyl}methylcarbamate (161 mg), 15-crown-5 (132 mg) and a solution of crude 4-methylpyridine-3-sulfonyl chloride (125 mg) in tetrahydrofuran (1 mL) at room temperature, and the mixture was stirred for 1 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=17:3→1:1) to give the title compound as a pale-yellow oil (yield 127 mg, 53%).

¹H-NMR (CDCl₃)δ: 1.49(9H,s), 2.36(3H,s), 2.92(3H,s), 4.32(2H,s), 7.19(1H,d,J=5.1 Hz), 7.23-7.31(1H,m), 7.41(1H, brs), 7.82(1H,dt,J=8.3,1.9 Hz), 8.18-8.26(2H,m), 8.58(1H,d, J=5.1 Hz).

Reference Example 26

3-(Benzylsulfanyl)-5-methylpyridine

To a solution of 3-bromo-5-methylpyridine (888 mg) in toluene (10 mL) were added phenylmethanethiol (705 mg), N,N-diisopropylethylamine (1.47 g), tris(dibenzylideneacetone)dipalladium(0) (189 mg) and 4,5-bis(diphenylphosphino)-9,9-dimethylxanthene (239 mg), and the mixture was stirred under an argon atmosphere at 80° C. for 1.5 hr. The reaction mixture was filtered through silica gel, and the filtrate was concentrated under reduced pressure. The residue was purified by silica gel column chromatography (eluent: hexane-ethyl acetate=19:1→17:3) to give the title compound as a yellow oil (yield 1.06 g, 95%).

¹H-NMR (CDCl₃)δ: 2.26(3H,d,J=0.8 Hz), 4.09(2H,s), 7.20-7.33(5H,m), 7.37(1H,dt,J=2.1,0.8 Hz), 8.25(1H,d,J=1.3 Hz), 8.33(1H,d,J=2.1 Hz).

Reference Example 27

5-Methylpyridine-3-sulfonyl chloride

To a solution of 3-(benzylsulfanyl)-5-methylpyridine (1.06 g) in acetic acid (15 mL)-water (5 mL) was added N-chlorosuccinimide (2.63 g) at room temperature and the mixture was stirred for 2 hr. The reaction mixture was concentrated under reduced pressure, diluted with water and extracted twice with ethyl acetate. Combined organic layers were washed with saturated brine, dried over anhydrous magnesium sulfate and concentrated under reduced pressure. The residue was purified by silica gel column chromatography (eluent:hexane-ethyl acetate=19:1→17:3) to give the title compound as a colorless oil (yield 700 mg, 74%).

$^1$H-NMR (CDCl$_3$)δ: 2.52(3H,s), 7.96-8.22(1H,m), 8.78 (1H,d,J=1.5 Hz), 9.06(1H,d,J=2.3 Hz).

Reference Example 28 tert-Butyl ({4-fluoro-5-(2-fluoropyridin-3-yl)-1-[(5-methylpyridin-3-yl)sulfonyl]-1H-pyrrol-3-yl}methyl)methylcarbamate To a suspension of sodium hydride (60% in oil, 24 mg) in tetrahydrofuran (3 mL) were added tert-butyl {[4-fluoro-5-(2-fluoropyridin-3-yl)-1H-pyrrol-3-yl]methyl}methylcarbamate (323 mg), 15-crown-5 (264 mg) and a solution of 4-methylpyridine-3-sulfonyl chloride (249 mg) in tetrahydrofuran (2 mL) at room temperature, and the mixture was stirred for 1 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent: hexane-ethyl acetate=9:1→1:1) to give the title compound as a pale-yellow oil (yield 370 mg, 77%).

$^1$H-NMR (CDCl$_3$)δ: 1.48(9H,s), 2.35(3H,d,J=0.4 Hz), 2.86(3H,s), 4.26(2H,brs), 7.26(1H,s), 7.32(1H,ddd,J=7.3, 5.2,1.5 Hz), 7.38(1H,brs), 7.76-7.90(1H,m), 8.25-8.34(1H, m), 8.46(1H,d,J=2.1 Hz), 8.63(1H,d,J=1.5 Hz).

Reference Example 29 tert-Butyl ({4-fluoro-5-(2-fluoropyridin-3-yl)-1-[(6-methylpyridin-3-yl)sulfonyl]-1H-pyrrol-3-yl}methyl)methylcarbamate To a suspension of sodium hydride (60% in oil, 31 mg) in tetrahydrofuran (3 mL) were added tert-butyl {[4-fluoro-5-(2-fluoropyridin-3-yl)-1H-pyrrol-3-yl]methyl}methylcarbamate (100 mg), 15-crown-5 (170 mg), 6-methylpyridine-3-sulfonyl chloride hydrochloride (91 mg) at room temperature, and the mixture was stirred for 1.5 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=17:31:1) to give the title compound as a pale-yellow oil (yield 123 mg, 83%).

$^1$H-NMR (CDCl$_3$)δ: 1.48(9H,s), 2.62(3H,s), 2.86(3H,s), 4.26(2H,s), 7.20(1H,d,J=8.0 Hz), 7.27-7.34(2H,m), 7.51(1H, dd,J=8.0,1.9 Hz), 7.76-7.86(1H,m), 8.27-8.36(1H,m), 8.50 (1H,d,J=2.3 Hz).

Reference Example 30

3-(Benzylsulfanyl)-2-methylpyridine

To a solution of 3-bromo-2-methylpyridine (1.0 g) in toluene (12 mL) were added phenylmethanethiol (794 mg), N,N-diisopropylethylamine (1.65 g), tris(dibenzylideneacetone) dipalladium(0) (213 mg) and 4,5-bis(diphenylphosphino)-9, 9-dimethylxanthene (269 mg), and the mixture was stirred under an argon atmosphere at 80° C. for 4 hr. The reaction mixture was filtered through silica gel, and the filtrate was concentrated under reduced pressure. The residue was purified by silica gel column chromatography (eluent:hexane-ethyl acetate=9:1→3:1) to give the title compound as a yellow solid (yield 742 mg, 59%).

$^1$H-NMR (CDCl$_3$)δ: 2.56(3H,s), 4.08(2H,s), 7.03(1H,dd, J=7.6,5.0 Hz), 7.21-7.34(5H,m), 7.48(1H,dd,J=7.8,1.6 Hz), 8.30(1H,dd,J=4.8,1.6 Hz).

Reference Example 31

2-Methylpyridine-3-sulfonyl chloride

To a solution of 3-(benzylsulfanyl)-2-methylpyridine (731 mg) in acetic acid (9 mL)-water (3 mL) was added N-chlorosuccinimide (1.81 g) at room temperature and the mixture was stirred for 4 hr. The reaction mixture was concentrated under reduced pressure, diluted with water and extracted twice with ethyl acetate. Combined organic layers were washed with saturated brine, dried over anhydrous magnesium sulfate and concentrated under reduced pressure.

The residue was purified by silica gel column chromatography (eluent:hexane-ethyl acetate=19:1→7:3) to give the title compound as a colorless oil (yield 175 mg, 27%).

$^1$H-NMR (CDCl$_3$)δ: 3.03(3H,s), 7.40(1H,dd,J=8.1,4.7 Hz), 8.33(1H,dd,J=8.1,1.7 Hz), 8.80(1H,dd,J=4.7,1.7 Hz).

Reference Example 32 tert-Butyl ({4-fluoro-5-(2-fluoropyridin-3-yl)-1-[(2-methylpyridin-3-yl)sulfonyl]-1H-pyrrol-3-yl}methyl)methylcarbamate To a suspension of sodium hydride (60% in oil, 34 mg) in tetrahydrofuran (2 mL) were added tert-butyl {[4-fluoro-5-(2-fluoropyridin-3-yl)-1H-pyrrol-3-yl]methyl}methylcarbamate (226 mg), 15-crown-5 (185 mg) and a solution of 2-methylpyridine-3-sulfonyl chloride (174 mg) in tetrahydrofuran (1 mL) at room temperature, and the mixture was stirred for 18 hr. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent: hexane-ethyl acetate=17:3→1:1) to give the title compound as a yellow oil (yield 288 mg, 86%).

$^1$H-NMR (CDCl$_3$)δ: 1.49(9H,s), 2.61(3H,s), 2.92(3H,s), 4.32(2H,s), 7.03(1H,dd,J=8.1,4.7 Hz), 7.21-7.26(1H,m), 7.34(1H,dd,J=8.1,1.7 Hz), 7.42(1H,brs), 7.79(1H,ddd,J=9.2, 7.3,2.1 Hz), 8.19-8.26(1H,m), 8.63(1H,dd,J=4.9,1.5 Hz).

Reference Example 33

2-(Benzylsulfanyl)-5-methoxypyridine

To a solution of 2-bromo-5-methoxypyridine (1.13 g) in toluene (15 mL) were added phenylmethanethiol (820 mg), N,N-diisopropylethylamine (1.71 g), tris(dibenzylideneacetone)dipalladium(0) (220 mg) and 4,5-bis(diphenylphosphino)-9,9-dimethylxanthene (278 mg), and the mixture was stirred under an argon atmosphere at 80° C. for 3 hr. The reaction mixture was filtered through silica gel, and the filtrate was concentrated under reduced pressure. The residue was purified by silica gel column chromatography (eluent: hexane-ethyl acetate=49:1→19:1) to give the title compound as a yellow oil (yield 1.47 g, quantitative).
$^1$H-NMR (CDCl$_3$)δ: 3.83(3H,s), 4.37(2H,s), 6.99-7.10 (2H,m), 7.19-7.31(3H,m), 7.33-7.40(2H,m), 8.21(1H,dd, J=2.6,0.9 Hz).

Reference Example 34

5-Methoxypyridine-2-sulfonyl chloride

To a solution of 2-(benzylsulfanyl)-5-methoxypyridine (1.47 g) in acetic acid (9 mL)-water (3 mL) was added N-chlorosuccinimide (3.20 g) at room temperature and the mixture was stirred for 2 hr. The reaction mixture was concentrated under reduced pressure, diluted with water and extracted twice with ethyl acetate. Combined organic layers were washed with saturated brine, dried over anhydrous magnesium sulfate and concentrated under reduced pressure. The residue was purified by silica gel column chromatography (eluent:hexane-ethyl acetate=19:1→17:3) to give the title compound as a colorless solid (yield 984 mg, 79%).
$^1$H-NMR (CDCl$_3$)δ: 4.00(3H,s), 7.38(1H,dd,J=8.9,2.8 Hz), 8.08(1H,d,J=8.7 Hz), 8.43(1H,d,J=2.8 Hz).

Reference Example 35 tert-Butyl ({4-fluoro-5-(2-fluoropyridin-3-yl)-1-[(5-methoxypyridin-2-yl)sulfonyl]-1H-pyrrol-3-yl}methyl)methylcarbamate To a suspension of sodium hydride (60% in oil, 168 mg) in tetrahydrofuran (10 mL) were added tert-butyl {[4-fluoro-5-(2-fluoropyridin-3-yl)-1H-pyrrol-3-yl]methyl}methylcarbamate (970 mg), 15-crown-5 (925 mg) and a solution of 5-methoxypyridine-2-sulfonyl chloride (984 mg) in tetrahydrofuran (15 mL) at room temperature, and the mixture was stirred for 30 min. The reaction mixture concentrated under reduced pressure to a half volume, diluted with water, and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=17:3→1:1) to give the title compound as a yellow oil (yield 1.38 g, 93%).
$^1$H-NMR (CDCl$_3$)δ: 1.47(9H,s), 2.87(3H,s), 3.91(3H,s), 4.26(2H,brs), 7.16(1H,dd,J=8.8,2.9 Hz), 7.24-7.30(1H,m), 7.32(1H,d,J=5.5 Hz), 7.52(1H,d,J=8.9 Hz), 7.87(1H,ddd, J=9.2,7.4,2.1 Hz), 8.23(1H,d,J=2.4 Hz), 8.26(1H,ddd,J=4.9, 1.9,0.9 Hz).

Reference Example 36

5-Chloropyridin-3-yl trifluoromethanesulfonate

To a solution of 5-chloropyridin-3-ol (1.30 g) in tetrahydrofuran (50 mL) were added triethylamine (1.21 g) and N-phenylbis(trifluoromethanesulfonimide) (3.93 g) at room temperature, and the mixture was stirred for 20 min. The reaction mixture was concentrated under reduced pressure, and the residue was diluted with ethyl acetate and washed with 1 mol/L hydrochloric acid. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=99:1→19:1) to give the title compound as a colorless oil (yield 1.73 g, 66%).
$^1$H-NMR (CDCl$_3$)δ: 7.69(1H,t,J=2.3 Hz), 8.52(1H,d, J=2.3 Hz), 8.64(1H,d,J=1.9 Hz).

Reference Example 37

3-(Benzylsulfanyl)-5-chloropyridine

To a solution of 5-chloropyridin-3-yl trifluoromethanesulfonate (1.73 g) in toluene (15 mL) were added phenylmethanethiol (861 mg), N,N-diisopropylethylamine (1.88 g), tris(dibenzylideneacetone)dipalladium(0) (121 mg) and 4,5-bis(diphenylphosphino)-9,9-dimethylxanthene (153 mg), and the mixture was stirred under an argon atmosphere at 80° C. for 3 hr. The reaction mixture was filtered through silica gel, and the filtrate was concentrated under reduced pressure. The residue was purified by silica gel column chromatography (eluent:hexane→hexane-ethyl acetate=19:1) to give the title compound as a yellow oil (yield 1.63 g, quantitative).
$^1$H-NMR (CDCl$_3$)δ: 4.12(2H,s), 7.21-7.36(5H,m), 7.53 (1H,t,J=2.1 Hz), 8.36(2H,d,J=1.9 Hz).

Reference Example 38

5-Chloropyridine-3-sulfonyl chloride

To a solution of 3-(benzylsulfanyl)-5-chloropyridine (1.63 g) in acetic acid (9 mL)-water (3 mL) was added N-chlorosuccinimide (3.53 g) at room temperature and the mixture was stirred for 2 hr. The reaction mixture was concentrated under reduced pressure, diluted with water and extracted twice with ethyl acetate. Combined organic layers were washed with saturated brine, dried over anhydrous magnesium sulfate and concentrated under reduced pressure. The residue was azeotropically distilled with toluene and purified by silica gel column chromatography (eluent:hexane-ethyl acetate=49:1→9:1) to give the title compound as a colorless oil (yield 1.26 g, 90%).
$^1$H-NMR (CDCl$_3$)δ: 8.29(1H,t,J=2.2 Hz), 8.91(1H,d, J=2.2 Hz), 9.12(1H,d,J=1.9 Hz).

Reference Example 39 tert-Butyl ({1-[(5-chloropyridin-3-yl)sulfonyl]-4-fluoro-5-(2-fluoropyridin-3-yl)-1H-pyrrol-3-yl}methyl)methylcarbamate To a suspension of sodium hydride (60% in oil, 52 mg) in tetrahydrofuran (3 mL) were added tert-butyl {[4-fluoro-5-(2-fluoropyridin-3-yl)-1H-pyrrol-3-yl]methyl}methylcarbamate (323 mg), 15-crown-5 (286 mg) and a solution of 5-chloropyridine-3-sulfonyl chloride (318 mg) in tetrahydrofuran (2 mL) at room temperature, and the mixture was stirred for 20 min. The reaction mixture was diluted with water and extracted with ethyl acetate. The separated aqueous layer was extracted again with ethyl acetate. Combined organic layers were washed with saturated brine, dried over anhydrous magnesium sulfate and concentrated under reduced pressure. The residue was purified by silica gel column chromatography (eluent:hexane-ethyl acetate=9:17:3) to give the title compound as a colorless oil (yield 391 mg, 78%).

$^1$H-NMR (CDCl$_3$)δ: 1.48(9H,s), 2.88(3H,s), 4.27(2H,s), 7.26(1H,s), 7.33(1H,ddd,J=7.3,5.2,1.5 Hz), 7.61(1H,t,J=2.1 Hz), 7.80(1H,ddd,J=9.2,7.5,1.9 Hz), 8.26-8.38(1H,m), 8.50 (1H,d,J=1.9 Hz), 8.76(1H,d,J=2.3 Hz).

Example 1

1-{4-Fluoro-5-(2-fluoropyridin-3-yl)-1-[(3-methylpyridin-2-yl)sulfonyl]-1H-pyrrol-3-yl}-N-methyl-methanamine fumarate To a solution of tert-butyl ({4-fluoro-5-(2-fluoropyridin-3-yl)-1-[(3-methylpyridin-2-yl)sulfonyl]-1H-pyrrol-3-yl}methyl)methylcarbamate (107 mg) in ethyl acetate (2 mL) and 2-propanol (1 mL) were added 4 mol/L hydrogen chloride-ethyl acetate solution (3 mL), and the mixture was stirred at room temperature for 1 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. Combined organic layers were washed with saturated brine, dried over anhydrous magnesium sulfate and concentrated under reduced pressure. The residue was purified by basic silica gel column chromatography (eluent:hexane-ethyl acetate=4:1→1:1) to give 1-{4-fluoro-5-(2-fluoropyridin-3-yl)-1-[(3-methylpyridin-2-yl)sulfonyl]-1H-pyrrol-3-yl}-N-methylmethanamine as a pale-yellow oil (yield 45 mg, 54%). A solution of the obtained 1-{4-fluoro-5-(2-fluoropyridin-3-yl)-1-[(3-methylpyridin-2-yl)sulfonyl]-1H-pyrrol-3-yl}-N-methylmethanamine in ethyl acetate (2 mL) was added dropwise to a solution of fumaric acid (14 mg) in ethanol (2 mL) and the mixture was concentrated under reduced pressure. The residue was recrystallized from ethyl acetate-ethanol to give the title compound as a white solid (yield 51 mg, 88%).

$^1$H-NMR (DMSO-d$_6$)δ: 2.35(3H,s), 2.38(3H,s), 3.73(2H, s), 6.53(2H,s), 7.32-7.39(1H,m), 7.48(1H,d,J=5.7 Hz), 7.63 (1H,dd,J=7.8,4.4 Hz), 7.74-7.83(1H,m), 7.93(1H,d,J=7.6 Hz), 8.27(1H,d,J=4.2 Hz), 8.41(1H,d,J=4.5 Hz), 3H not detected.

Example 2

1-{4-Fluoro-5-(2-fluoropyridin-3-yl)-1-[(4-methylpyridin-2-yl)sulfonyl]-1H-pyrrol-3-yl}-N-methyl-methanamine hydrochloride To a solution of tert-butyl ({4-fluoro-5-(2-fluoropyridin-3-yl)-1-[(4-methylpyridin-2-yl)sulfonyl]-1H-pyrrol-3-yl}methyl)methylcarbamate (333 mg) in ethyl acetate (2 mL) and 2-propanol (1 mL) was added 4 mol/L hydrogen chloride-ethyl acetate solution (3 mL), and the mixture was stirred at room temperature for 1 hr. The reaction mixture was concentrated under reduced pressure, and the residue was recrystallized from ethyl acetate-ethanol to give the title compound as a white solid (yield 191 mg, 66%).

$^1$H-NMR (DMSO-d$_6$)δ: 2.37(3H,s), 2.56(3H,s), 4.05(2H, s), 7.45(1H,ddd,J=7.3,5.0,1.7 Hz), 7.54(1H,s), 7.59-7.66(1H, m), 7.77-7.90(2H,m), 8.33-8.40(1H,m), 8.55(1H,d,J=4.9 Hz), 9.11(2H,brs).

Example 3

1-{4-Fluoro-5-(2-fluoropyridin-3-yl)-1-[(5-fluoropyridin-2-yl)sulfonyl]-1H-pyrrol-3-yl}-N-methyl-methanamine hydrochloride To a solution of tert-butyl ({4-fluoro-5-(2-fluoropyridin-3-yl)-1-[(5-fluoropyridin-2-yl)sulfonyl]-1H-pyrrol-3-yl}methyl)methylcarbamate (69 mg) in ethyl acetate (1.5 mL) and 2-propanol (1 mL) was added 4 mol/L hydrogen chloride-ethyl acetate solution (2 mL), and the mixture was stirred at room temperature for 2.5 hr. The reaction mixture was concentrated under reduced pressure, and the residue was recrystallized from ethyl acetate-ethanol to give the title compound as a white solid (yield 31 mg, 51%).

$^1$H-NMR (DMSO-d$_6$)δ: 2.58(3H,s), 4.07(2H,s), 7.41-7.49 (1H,m), 7.80(1H,d,J=5.5 Hz), 7.82-7.91(2H,m), 8.05(1H,dt, J=8.6,2.8 Hz), 8.36(1H,ddd,J=4.9,1.9,0.9 Hz), 8.78(1H,d, J=2.8 Hz), 8.97(2H,brs).

Example 4

1-{4-Fluoro-5-(2-fluoropyridin-3-yl)-1-[(4-methoxypyridin-2-yl)sulfonyl]-1H-pyrrol-3-yl}-N-methyl-methanamine hydrochloride To a solution of tert-butyl ({4-fluoro-5-(2-fluoropyridin-3-yl)-1-[(4-methoxypyridin-2-yl)sulfonyl]-1H-pyrrol-3-yl}methyl)methylcarbamate (94 mg) in ethyl acetate (2 mL) and 2-propanol (1 mL) was added 4 mol/L hydrogen chloride-ethyl acetate solution (2 mL), and the mixture was stirred at room temperature for 4 hr. The reaction mixture was concentrated under reduced pressure, and the residue was recrystallized from ethyl acetate-ethanol to give the title compound as a white solid (yield 65 mg, 79%).

$^1$H-NMR (DMSO-d$_6$)δ: 2.57(3H,s), 3.87(3H,s), 4.06(2H, s), 7.17(1H,d,J=2.3 Hz), 7.33(1H,dd,J=5.7,2.7 Hz), 7.46(1H, ddd,J=6.9,5.2,1.5 Hz), 7.80(1H,d,J=5.7 Hz), 7.89(1H,ddd, J=9.3,7.6,1.7 Hz), 8.30-8.39(1H,m), 8.51(1H,d,J=5.7 Hz), 9.01(2H,brs).

Example 5

1-{4-Fluoro-5-(2-fluoropyridin-3-yl)-1-[(5-fluoropyridin-3-yl)sulfonyl]-1H-pyrrol-3-yl}-N-methyl-methanamine hydrochloride To a solution of tert-butyl ({4-fluoro-5-(2-fluoropyridin-3-yl)-1-[(5-fluoropyridin-3-yl)sulfonyl]-1H-pyrrol-3-yl}methyl)methylcarbamate (224 mg) in ethyl acetate (2 mL) and 2-propanol (1 mL) was added 4N hydrogen chloride-ethyl acetate solution (3 mL), and the mixture was stirred at room temperature for 3 hr. The reaction mixture was concentrated under reduced pressure, and the residue was recrystallized from ethyl acetate-ethanol to give the title compound as a white solid (yield 127 mg, 65%).

$^1$H-NMR (DMSO-d$_6$)δ: 2.58(3H,s), 4.05(2H,s), 7.46-7.55 (1H,m), 7.87-7.97(2H,m), 8.03(1H,dt,J=7.6,2.3 Hz), 8.42 (1H,d,J=4.2 Hz), 8.49(1H,s), 9.04(1H,d,J=2.3 Hz), 9.09(2H, brs).

Example 6

1-{4-Fluoro-5-(2-fluoropyridin-3-yl)-1-[(4-methylpyridin-3-yl)sulfonyl]-1H-pyrrol-3-yl}-N-methylmethanamine fumarate To a solution of tert-butyl ({4-fluoro-5-(2-fluoropyridin-3-yl)-1-[(4-methylpyridin-3-yl)sulfonyl]-1H-pyrrol-3-yl}methyl)methylcarbamate (127 mg) in ethyl acetate (2 mL) and 2-propanol (0.5 mL) was added 4N hydrogen chloride-ethyl acetate solution (2 mL), and the mixture was stirred at room temperature for 2 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. Combined organic layers were washed with saturated brine, dried over anhydrous magnesium sulfate and concentrated under reduced pressure to give 1-{4-fluoro-5-(2-fluoropyridin-3-yl)-1-[(4-methylpyridin-3-yl)sulfonyl]-1H-pyrrol-3-yl}-N-methylmethanamine as a pale-yellow oil (yield 97 mg, 97%). A solution of the obtained 1-{4-fluoro-5-(2-fluoropyridin-3-yl)-1-[(4-methylpyridin-3-yl)sulfonyl]-1H-pyrrol-3-yl}-N-methylmethanamine in ethyl acetate (2 mL) was added dropwise to a solution of fumaric acid (30 mg) in ethanol (2 mL) and concentrated under reduced pressure. The residue was recrystallized from ethanol to give the title compound as a white solid (yield 103 mg, 81%).

$^1$H-NMR (DMSO-$d_6$)δ: 2.33(3H,s), 2.40(3H,s), 3.76(2H, s), 6.53(2H,s), 7.43(1H,ddd,J=7.3,5.1,1.8 Hz), 7.52(1H,d, J=5.1 Hz), 7.72(1H,d,J=5.7 Hz), 7.85(1H,ddd,J=9.5,7.4,1.9 Hz), 8.14(1H,s), 8.32(1H,ddd,J=4.9,1.9,0.9 Hz), 8.70(1H,d, J=5.1 Hz), 3H not detected.

Example 7

1-{4-Fluoro-5-(2-fluoropyridin-3-yl)-1-[(5-methylpyridin-3-yl)sulfonyl]-1H-pyrrol-3-yl}-N-methylmethanamine fumarate To a solution of tert-butyl ({4-fluoro-5-(2-fluoropyridin-3-yl)-1-[(5-methylpyridin-3-yl)sulfonyl]-1H-pyrrol-3-yl}methyl)methylcarbamate (370 mg) in ethyl acetate (2 mL) and 2-propanol (1 mL) was added 4N hydrogen chloride-ethyl acetate solution (3 mL), and the mixture was stirred at room temperature for 3 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. Combined organic layers were washed with saturated brine, dried over anhydrous magnesium sulfate and concentrated under reduced pressure to give 1-{4-fluoro-5-(2-fluoropyridin-3-yl)-1-[(5-methylpyridin-3-yl)sulfonyl]-1H-pyrrol-3-yl}-N-methylmethanamine as a pale-yellow oil (yield 256 mg, 88%). A solution of the obtained 1-{4-fluoro-5-(2-fluoropyridin-3-yl)-1-[(5-methylpyridin-3-yl)sulfonyl]-1H-pyrrol-3-yl}-N-methylmethanamine in ethyl acetate (2 mL) was added dropwise to a solution of fumaric acid (78 mg) in ethanol (2 mL) and concentrated under reduced pressure. The residue was recrystallized from ethanol-water to give the title compound as a white solid (yield 288 mg, 87%).

$^1$H-NMR (DMSO-$d_6$)δ: 2.33(3H,s), 2.35(3H,s), 3.70(2H, s), 6.54(2H,s), 7.50(1H,ddd,J=7.3,5.1,1.9 Hz), 7.63-7.71(2H, m), 7.90(1H,ddd,J=9.6,7.5,2.0 Hz), 8.36-8.41(1H,m), 8.42 (1H,d,J=2.3 Hz), 8.76(1H,d,J=1.3 Hz), 3H not detected.

Example 8

1-{4-Fluoro-5-(2-fluoropyridin-3-yl)-1-[(6-methylpyridin-3-yl)sulfonyl]-1H-pyrrol-3-yl}-N-methylmethanamine 0.5 fumarate To a solution of tert-butyl ({4-fluoro-5-(2-fluoropyridin-3-yl)-1-[(6-methylpyridin-3-yl)sulfonyl]-1H-pyrrol-3-yl}methyl)methylcarbamate (123 mg) in ethyl acetate (2 mL) and 2-propanol (1 mL) was added 4 mol/L hydrogen chloride-ethyl acetate solution (3 mL), and the mixture was stirred at room temperature for 3 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. Combined organic layers were washed with saturated brine, dried over anhydrous magnesium sulfate and concentrated under reduced pressure. The residue was purified by basic silica gel column chromatography (eluent:hexane-ethyl acetate=1:1) to give 1-{4-fluoro-5-(2-fluoropyridin-3-yl)-1-[(6-methylpyridin-3-yl)sulfonyl]-1H-pyrrol-3-yl}-N-methylmethanamine as a colorless oil (yield 88 mg, 91%). A solution of the obtained 1-{4-fluoro-5-(2-fluoropyridin-3-yl)-1-[(6-methylpyridin-3-yl)sulfonyl]-1H-pyrrol-3-yl}-N-methylmethanamine in ethyl acetate (2 mL) was added dropwise to a solution of fumaric acid (27 mg) in ethanol (2 mL) and concentrated under reduced pressure. The residue was recrystallized from ethanol-water to give the title compound as a white solid (yield 78 mg, 77%).

$^1$H-NMR (DMSO-$d_6$)δ: 2.30(3H,s), 2.56(3H,s), 3.61(2H, s), 6.51(1H,s), 7.45-7.53(2H,m), 7.60(1H,d,J=5.7 Hz), 7.79 (1H,dd,J=8.3,2.3 Hz), 7.91(1H,ddd,J=9.6,7.5,1.9 Hz), 8.35-8.40(1H,m), 8.48(1H,d,J=2.3 Hz), 2H not detected.

Example 9

1-{4-Fluoro-5-(2-fluoropyridin-3-yl)-1-[(2-methylpyridin-3-yl)sulfonyl]-1H-pyrrol-3-yl}-N-methylmethanamine fumarate To a solution of tert-butyl ({4-fluoro-5-(2-fluoropyridin-3-yl)-1-[(2-methylpyridin-3-yl)sulfonyl]-1H-pyrrol-3-yl}methyl)methylcarbamate (288 mg) in ethyl acetate (2 mL) and 2-propanol (1 mL) was added 4 mol/L hydrogen chloride-ethyl acetate solution (3 mL), and the mixture was stirred at room temperature for 3 hr. The reaction mixture was concentrated under reduced pressure, and the residue was diluted with saturated aqueous sodium hydrogen carbonate solution, and extracted with ethyl acetate. The separated aqueous layer was extracted again with ethyl acetate. Combined organic layers were washed with saturated brine, dried over anhydrous magnesium sulfate and concentrated under reduced pressure to give 1-{4-fluoro-5-(2-fluoropyridin-3-yl)-1-[(2-methylpyridin-3-yl)sulfonyl]-1H-pyrrol-3-yl}-N-methylmethanamine as a colorless oil (yield 220 mg, 97%). A solution of the obtained 1-{4-fluoro-5-(2-fluoropyridin-3-yl)-1-[(2-methylpyridin-3-yl)sulfonyl]-1H-pyrrol-3-yl}-N-methylmethanamine in ethyl acetate (3 mL) was added dropwise to a solution of fumaric acid (67 mg) in ethanol (3 mL) and concentrated under reduced pressure. The residue was recrystallized from ethanol to give the title compound as a white solid (yield 253 mg, 88%).

¹H-NMR (DMSO-d₆)δ: 2.41(3H,s), 2.49(3H,s), 3.77(2H, s), 6.53(2H,s), 7.31(1H,dd,J=8.1,4.7 Hz), 7.42(1H,ddd, J=7.2,5.1,1.7 Hz), 7.47(1H,dd,J=8.3,1.5 Hz), 7.71(1H,d, J=5.7 Hz), 7.84(1H,ddd,J=9.6,7.5,1.9 Hz), 8.28-8.34(1H,m), 8.73(1H,dd,J=4.7,1.7 Hz), 3H not detected.

Example 10

1-{4-Fluoro-5-(2-fluoropyridin-3-yl)-1-[(5-methoxypyridin-2-yl)sulfonyl]-1H-pyrrol-3-yl}-N-methylmethanamine hydrochloride To a solution of tert-butyl ({4-fluoro-5-(2-fluoropyridin-3-yl)-1-[(5-methoxypyridin-2-yl)sulfonyl]-1H-pyrrol-3-yl}methyl)methylcarbamate (1.38 g) in ethyl acetate (6 mL) and 2-propanol (3 mL) was added 4 mol/L hydrogen chloride-ethyl acetate solution (9 mL), and the mixture was stirred at room temperature for 1.5 hr. The reaction mixture was concentrated under reduced pressure, and the residue was recrystallized from ethanol-water to give the title compound as a white solid (yield 1.06 g, 88%).
¹H-NMR (DMSO-d₆)δ: 2.54(3H,s), 3.91(3H,s), 4.03(2H, s), 7.38-7.46(1H,m), 7.51-7.58(1H,m), 7.62-7.70(1H,m), 7.75-7.87(2H,m), 8.33(1H,dt,J=4.7,0.8 Hz), 8.36(1H,d,J=3.0 Hz), 9.20(2H,brs).

Example 11

1-{1-[(5-Chloropyridin-3-yl)sulfonyl]-4-fluoro-5-(2-fluoropyridin-3-yl)-1H-pyrrol-3-yl}-N-methylmethanamine hydrochloride To a solution of tert-butyl ({1-[(5-chloropyridin-3-yl)sulfonyl]-4-fluoro-5-(2-fluoropyridin-3-yl)-1H-pyrrol-3-yl}methyl)methylcarbamate (391 mg) in ethyl acetate (2 mL) and 2-propanol (1 mL) was added 4 mol/L hydrogen chloride-ethyl acetate solution (3 mL), and the mixture was stirred at room temperature for 1.5 hr. The reaction mixture was concentrated under reduced pressure, and the residue was recrystallized from ethanol to give the title compound as a white solid (yield 298 mg, 95%).
¹H-NMR (DMSO-d₆)δ: 2.57(3H,s), 4.05(2H,s), 7.52(1H, ddd,J=7.3,5.1,1.9 Hz), 7.93(1H,ddd,J=9.6,7.5,2.0 Hz), 8.01 (1H,d,J=5.5 Hz), 8.11(1H,t,J=2.2 Hz), 8.43(1H,ddd,J=4.9, 1.8,0.8 Hz), 8.57(1H,d,J=2.1 Hz), 9.05(1H,d,J=2.1 Hz), 9.33 (2H,brs).

Example 12

1-{4-Fluoro-1-[(5-fluoro-6-methylpyridin-2-yl)sulfonyl]-5-(2-fluoropyridin-3-yl)-1H-pyrrol-3-yl}-N-methylmethanamine The compound is synthesized in the same manner as in Reference Example 15, Reference Example 16, Reference Example 17 and Example 3 and using 6-bromo-3-fluoro-2-methylpyridine.

Example 13

1-{4-Fluoro-1-[(5-fluoro-4-methylpyridin-2-yl)sulfonyl]-5-(2-fluoropyridin-3-yl)-1H-pyrrol-3-yl}-N-methylmethanamine The compound is synthesized in the same manner as in Reference Example 15, Reference Example 16, Reference Example 17 and Example 3 and using 2-bromo-5-fluoro-4-methylpyridine.

Example 14

1-{4-Fluoro-1-[(5-fluoro-4-methoxypyridin-2-yl)sulfonyl]-5-(2-fluoropyridin-3-yl)-1H-pyrrol-3-yl}-N-methylmethanamine tert-Butyl group is removed from 4-tert-butoxy-2,5-difluoropyridine, and the resulting compound is methylated to give 2,5-difluoro-4-methoxypyridine, which is then subjected to synthesis in the same manner as in Reference Example 15, Reference Example 16, Reference Example 17 and Example 3.

Example 15

1-{4-Fluoro-5-(2-fluoropyridin-3-yl)-1-[(5-methoxypyridin-3-yl)sulfonyl]-1H-pyrrol-3-yl}-N-methylmethanamine The compound is synthesized in the same manner as in Reference Example 20, Reference Example 21, Reference Example 22 and Example 5 and using 3-bromo-5-methoxypyridine.

Example 16

1-{4-Fluoro-1-[(5-fluoro-6-methylpyridin-3-yl)sulfonyl]-5-(2-fluoropyridin-3-yl)-1H-pyrrol-3-yl}-N-methylmethanamine 5-Chloro-3-fluoro-2-methylpyridine is synthesized from 5-chloro-3-fluoro-2-iodopyridine by a boronic acid coupling reaction and the resulting compound is subjected to synthesis in the same manner as in Reference Example 20, Reference Example 21, Reference Example 22 and Example 5.

Example 17

1-{1-[(4,6-Dimethylpyridin-2-yl)sulfonyl]-4-fluoro-5-(2-fluoropyridin-3-yl)-1H-pyrrol-3-yl}-N-methylmethanamine The compound is synthesized in the same manner as in Reference Example 15, Reference Example 16, Reference Example 17 and Example 3 and using 2-bromo-4,6-dimethylpyridine.

Example 18

1-{1-[(5-Chloropyridin-2-yl)sulfonyl]-4-fluoro-5-(2-fluoropyridin-3-yl)-1H-pyrrol-3-yl}-N-methylmethanamine The compound is synthesized in the same manner as in Reference Example 17 and Example 3 and using 5-chloropyridine-2-sulfonyl chloride.

Example 19

1-{1-[(5,6-Dimethylpyridin-2-yl)sulfonyl]-4-fluoro-5-(2-fluoropyridin-3-yl)-1H-pyrrol-3-yl}-N-methylmethanamine The compound is synthesized in the same manner as in Reference Example 15, Reference Example 16, Reference Example 17 and Example 3 and using 6-bromo-2,3-dimethylpyridine.

Example 20

1-{1-[(4,5-Dimethylpyridin-2-yl)sulfonyl]-4-fluoro-5-(2-fluoropyridin-3-yl)-1H-pyrrol-3-yl}-N-methyl-methanamine The compound is synthesized in the same manner as in Reference Example 15, Reference Example 16, Reference Example 17 and Example 3 and using 2-bromo-4,5-dimethylpyridine.

Example 21

1-{4-Fluoro-5-(2-fluoropyridin-3-yl)-1-[(4-methylpyridin-2-yl)sulfonyl]-1H-pyrrol-3-yl}-N-methyl-methanamine 1-{4-Fluoro-5-(2-fluoropyridin-3-yl)-1-[(4-methylpyridin-2-yl)sulfonyl]-1H-pyrrol-3-yl}-N-methylmethanamine hydrochloride (751 mg) was dissolved in saturated aqueous sodium hydrogen carbonate, and extracted twice with ethyl acetate. Combined organic layers were washed with saturated brine, dried over anhydrous magnesium sulfate and concentrated under reduced pressure to give the title compound as a pale-yellow oil (yield 647 mg, 95%).
$^1$H-NMR (CDCl$_3$)δ: 2.38(3H,s), 2.45(3H,s), 3.64(2H,s), 7.23-7.30(2H,m), 7.33(1H,d,J=5.7 Hz), 7.36(1H,s), 7.88(1H,ddd,J=9.3,7.4,1.9 Hz), 8.22-8.29(1H,m), 8.45(1H,d,J=4.5 Hz), 1H not detected.

Example 22

1-{4-Fluoro-5-(2-fluoropyridin-3-yl)-1-[(5-fluoropyridin-3-yl)sulfonyl]-1H-pyrrol-3-yl}-N-methyl-methanamine 1-{4-Fluoro-5-(2-fluoropyridin-3-yl)-1-[(5-fluoropyridin-3-yl)sulfonyl]-1H-pyrrol-3-yl}-N-methylmethanamine (780 mg) was dissolved in saturated aqueous sodium hydrogen carbonate, and the mixture was extracted twice with ethyl acetate. Combined organic layers were washed with saturated brine, dried over anhydrous magnesium sulfate and concentrated under reduced pressure. The residue was purified by basic silica gel column chromatography (eluent:hexane-ethyl acetate=3:1→3:7) to give the title compound as a pale-yellow oil (yield 619 mg, 87%).
$^1$H-NMR (CDCl$_3$)δ: 2.46(3H,s), 3.65(2H,s), 7.28-7.36 (2H,m), 7.41(1H,dt,J=7.3,2.2 Hz), 7.80(1H,ddd,J=9.2,7.4,2.0 Hz), 8.28-8.39(1H,m), 8.48(1H,s), 8.68(1H,d,J=2.6 Hz), 1H not detected.

Example 23

1-{4-Fluoro-5-(2-fluoropyridin-3-yl)-1-[(4-methylpyridin-2-yl)sulfonyl]-1H-pyrrol-3-yl}-N-methyl-methanamine fumarate To a solution of fumaric acid (58 mg) in ethanol (2 mL) was added a solution of 1-{4-fluoro-5-(2-fluoropyridin-3-yl)-1-[(4-methylpyridin-2-yl)sulfonyl]-1H-pyrrol-3-yl}-N-methylmethanamine (189 mg) in ethyl acetate (2 mL), and the mixture was concentrated under reduced pressure. The residue was recrystallized from ethanol to give the title compound as a white solid (yield 224 mg, 91%).
$^1$H-NMR (DMSO-d$_6$)δ: 2.35-2.40(6H,m), 3.73(2H,s), 6.53(2H,s), 7.44(1H,ddd,J=7.3,5.1,1.8 Hz), 7.49-7.55(2H, m), 7.59(1H,d,J=4.9 Hz), 7.86(1H,ddd,J=9.5,7.4,1.9 Hz), 8.27-8.39(1H,m), 8.54(1H,d,J=4.9 Hz), 3H not detected.

Example 24

1-{4-Fluoro-5-(2-fluoropyridin-3-yl)-1-[(4-methylpyridin-2-yl)sulfonyl]-1H-pyrrol-3-yl}-N-methyl-methanamine succinate To a solution of succinic acid (59 mg) in ethanol (2 mL) was added a solution of 1-{4-fluoro-5-(2-fluoropyridin-3-yl)-1-[(4-methylpyridin-2-yl)sulfonyl]-1H-pyrrol-3-yl}-N-methylmethanamine (189 mg) in ethyl acetate (2 mL) and the mixture was concentrated under reduced pressure. The residue was recrystallized from ethanol-water to give the title compound as a white solid (yield 232 mg, 93%).
$^1$H-NMR (DMSO-d$_6$)δ: 2.34(3H,s), 2.36(4H,s), 2.37(3H,s), 3.66(2H,s), 7.39-7.49(2H,m), 7.52(1H,s), 7.55-7.63(1H, m), 7.86(1H,ddd,J=9.5,7.4,1.9 Hz), 8.34(1H,ddd,J=4.9,1.9,0.9 Hz), 8.54(1H,d,J=4.9 Hz), 3H not detected.

Example 25

1-{4-Fluoro-5-(2-fluoropyridin-3-yl)-1-[(5-fluoropyridin-3-yl)sulfonyl]-1H-pyrrol-3-yl}-N-methyl-methanamine 0.5 fumarate To a solution of fumaric acid (36 mg) in ethanol (2 mL) was added a solution of 1-{4-fluoro-5-(2-fluoropyridin-3-yl)-1-[(5-fluoropyridin-3-yl)sulfonyl]-1H-pyrrol-3-yl}-N-methylmethanamine (120 mg) in ethyl acetate (2 mL) and the mixture was concentrated under reduced pressure. The residue was recrystallized from ethanol to give the title compound as a white solid (yield 113 mg, 82%).
$^1$H-NMR (DMSO-d$_6$)δ: 2.32(3H,s), 3.63(2H,s), 6.52(1H, s), 7.50(1H,ddd,J=7.3,5.1,1.9 Hz), 7.67(1H,d,J=5.7 Hz), 7.94 (1H,ddd,J=9.6,7.5,2.0 Hz), 7.98-8.05(1H,m), 8.31-8.42(1H, m), 8.48(1H,s), 9.00(1H,d,J=2.8 Hz), 2H not detected.

Example 26

1-{4-Fluoro-5-(2-fluoropyridin-3-yl)-1-[(5-fluoropyridin-3-yl)sulfonyl]-1H-pyrrol-3-yl}-N-methyl-methanamine succinate A solution of succinic acid (46 mg) in ethanol (4 mL) was added to 1-{4-fluoro-5-(2-fluoropyridin-3-yl)-1-[(5-fluoropyridin-3-yl)sulfonyl]-1H-pyrrol-3-yl}-N-methylmethanamine (150 mg), and the mixture was concentrated under reduced pressure. The residue was recrystallized from ethanol to give the title compound as a white solid (yield 167 mg, 85%).
$^1$H-NMR (DMSO-d$_6$)δ: 2.33(3H,s), 2.38(4H,s), 3.64(2H, s), 7.50(1H,ddd,J=7.2,5.0,1.9 Hz), 7.66(1H,d,J=5.7 Hz), 7.94 (1H,ddd,J=9.6,7.5,2.0 Hz), 7.98-8.03(1H,m), 8.34-8.42(1H, m), 8.44-8.53(1H,m), 9.01(1H,d,J=2.6 Hz), 3H not detected.

Example 27

1-{4-Fluoro-5-(2-fluoropyridin-3-yl)-1-[(5-fluoropyridin-3-yl)sulfonyl]-1H-pyrrol-3-yl}-N-methyl-methanamine L-tartrate A solution of L-tartaric acid (59 mg) in ethanol (4 mL) was added to 1-{4-fluoro-5-(2-fluoropyridin-3-yl)-1-[(5-fluoropyridin-3-yl)sulfonyl]-1H-pyrrol-3-yl}-N-methylmethanamine (150 mg), and the mixture was concentrated under reduced pressure. The residue was recrystallized from ethanol to give the title compound as a white solid (yield 184 mg, 88%).

$^1$H-NMR (DMSO-$d_6$)δ: 2.44(3H,s), 3.81(2H,s), 4.00(2H, s), 7.51(1H,ddd,J=7.3,5.2,1.9 Hz), 7.75(1H,d,J=5.7 Hz), 7.93 (1H,ddd,J=9.5,7.4,1.9 Hz), 8.00(1H,dt,J=7.8,2.3 Hz), 8.38-8.43(1H,m), 8.49(1H,s), 9.02(1H,d,J=2.6 Hz), 5H not detected.

The structures of the compounds described in Reference Examples are shown in Tables 1-2.

TABLE 1

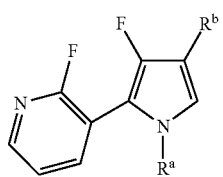

| Ref. Ex. No. | R$^a$ | R$^b$ |
|---|---|---|
| 5 | H | H |
| 6 | triisopropylsilyl (Si(iPr)$_3$-like, Me/Me/Me/Me/Me/Me groups) | H |
| 7 | H | CHO |
| 8 | H | CH$_2$N(Me)Boc |
| 11 | 3-methyl-2-(methylsulfonyl)pyridin-yl | CH$_2$N(Me)Boc |
| 14 | 4-methyl-2-(methylsulfonyl)pyridin-yl | CH$_2$N(Me)Boc |
| 17 | 5-fluoro-2-(methylsulfonyl)pyridin-yl | CH$_2$N(Me)Boc |
| 19 | 4-methoxy-2-(methylsulfonyl)pyridin-yl | CH$_2$N(Me)Boc |
| 22 | 5-fluoro-3-(methylsulfonyl)pyridin-yl | CH$_2$N(Me)Boc |

TABLE 1-continued

| Ref. Ex. No. | R$^a$ | R$^b$ |
|---|---|---|
| 25 | 4-methyl-3-(methylsulfonyl)pyridin-yl | CH$_2$N(Me)Boc |
| 28 | 5-methyl-3-(methylsulfonyl)pyridin-yl | CH$_2$N(Me)Boc |
| 29 | 6-methyl-3-(methylsulfonyl)pyridin-yl | CH$_2$N(Me)Boc |
| 32 | 2-methyl-3-(methylsulfonyl)pyridin-yl | CH$_2$N(Me)Boc |
| 35 | 5-methoxy-2-(methylsulfonyl)pyridin-yl | CH$_2$N(Me)Boc |
| 39 | 5-chloro-3-(methylsulfonyl)pyridin-yl | CH$_2$N(Me)Boc |

TABLE 2

Structural formulas of Reference Examples 1-4

| | |
|---|---|
| Boc-NH-CH$_2$-CHO | 1 |
| Boc-NH-CH$_2$-CH(OTs)-C(F)(F)-CO$_2$Et | 2 |
| 3-fluoro-3-fluoro-4-OTs-1-Boc-pyrrolidin-2-one | 3 |

TABLE 2-continued
| | |
|---|---|
| 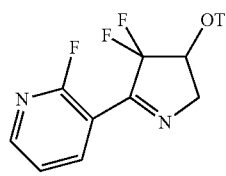 | 4 |
Other structural formulas of Reference Examples 9-39
| | |
|---|---|
| 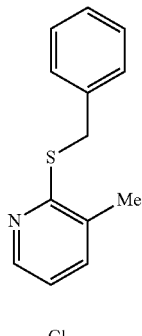 | 9 |
| 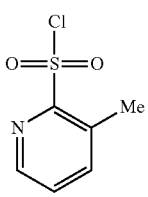 | 10 |
| 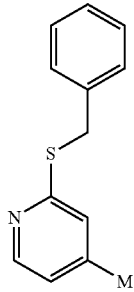 | 12 |
| 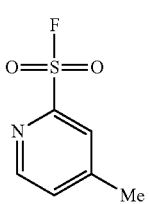 [SMILES: Cc1ccnc(S(=O)(=O)F)c1] | 13 |
| 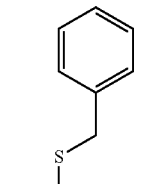 | 15 |
TABLE 2-continued
| | |
|---|---|
| 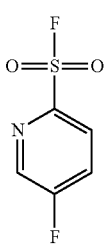 | 16 |
| 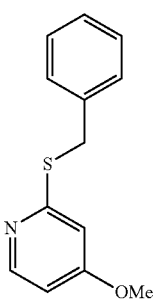 [SMILES: COc1ccnc(SCc2ccccc2)c1] | 18 |
| 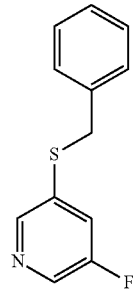 [SMILES: Fc1cncc(SCc2ccccc2)c1] | 20 |
| 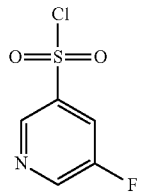 [SMILES: O=S(=O)(Cl)c1cncc(F)c1] | 21 |
| 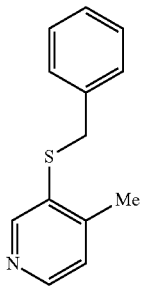 [SMILES: Cc1ccncc1SCc1ccccc1] | 23 |
| 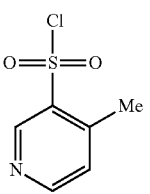 [SMILES: Cc1ccncc1S(=O)(=O)Cl] | 24 |

TABLE 2-continued
| | |
|---|---|
| 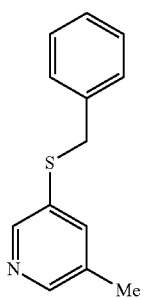 [SMILES: Cc1cncc(SCc2ccccc2)c1] | 26 |
| 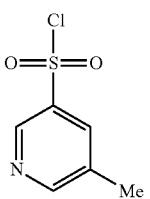 [SMILES: Cc1cncc(S(=O)(=O)Cl)c1] | 27 |
| 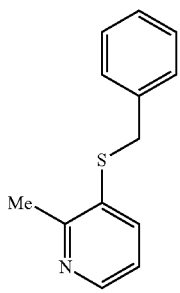 [SMILES: Cc1ncccc1SCc1ccccc1] | 30 |
| 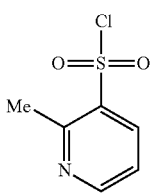 | 31 |
| 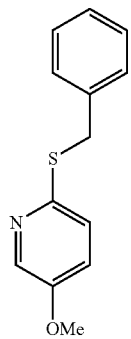 [SMILES: COc1ccc(SCc2ccccc2)nc1] | 33 |
| 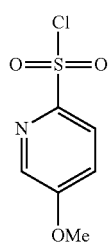 | 34 |
TABLE 2-continued
| | |
|---|---|
| 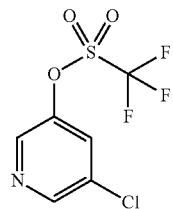 [SMILES: O=S(=O)(Oc1cncc(Cl)c1)C(F)(F)F] | 36 |
| 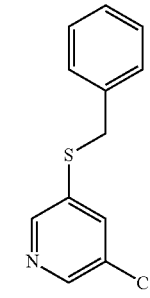 | 37 |
| 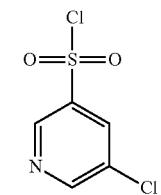 | 38 |
The structures of the compounds described in Examples are shown in Table 3.
TABLE 3
| Ex. No. | A | addition salt |
|---|---|---|
| 1 | ![pyridine with SO2Me and Me] | HO2C–CH=CH–CO2H |
| 2 | ![4-Me pyridine with SO2Me] | HCl |
| 3 | ![5-F pyridine with SO2Me] | HCl |
| 4 | ![4-OMe pyridine with SO2Me] | HCl |

TABLE 3-continued

Common structure: pyrrole with N-substituent A, 2-(2-fluoropyridin-3-yl), 3-fluoro, 4-(methylaminomethyl)

| Ex. No. | A | addition salt |
|---|---|---|
| 5 | 5-fluoro-3-(methylsulfonyl)pyridin-2-yl | HCl |
| 6 | 3-methyl-2-(methylsulfonyl)pyridin-?-yl (methyl at 3, SO2Me at 2) | HO2C-CH=CH-CO2H |
| 7 | 5-methyl-3-(methylsulfonyl)pyridin-2-yl | HO2C-CH=CH-CO2H |
| 8 | 6-methyl-3-(methylsulfonyl)pyridin-2-yl | HO2C-CH=CH-CO2H, 0.5 |
| 9 | 2-methyl-3-(methylsulfonyl)pyridin-?-yl | HO2C-CH=CH-CO2H |
| 10 | 5-methoxy-2-(methylsulfonyl)pyridin-?-yl | HCl |
| 11 | 5-chloro-3-(methylsulfonyl)pyridin-2-yl | HCl |
| 21 | 4-methyl-2-(methylsulfonyl)pyridin-?-yl | — |
| 22 | 4-fluoro-3-(methylsulfonyl)pyridin-?-yl | — |
| 23 | 4-methyl-2-(methylsulfonyl)pyridin-?-yl | HO2C-CH=CH-CO2H |
| 24 | 4-methyl-2-(methylsulfonyl)pyridin-?-yl | HO2C-CH2-CH2-CO2H |
| 25 | 5-fluoro-3-(methylsulfonyl)pyridin-2-yl | HO2C-CH=CH-CO2H, 0.5 |
| 26 | 5-fluoro-3-(methylsulfonyl)pyridin-2-yl | HO2C-CH2-CH2-CO2H |
| 27 | 5-fluoro-3-(methylsulfonyl)pyridin-2-yl | (2R,3R)-tartaric acid: HO-CH(CO2H)-CH(OH)-CO2H |

Experimental Example 1

Proton Potassium—Adenosine Triphosphatase ($H^+,K^+$-ATPase) Inhibitory Activity Test According to the method [Biochim. Biophys. Acta, 728, 31 (1983)] of Wallmark et al., a gastric mucous membrane microsomal fraction was prepared from the stomach of swine. First, the stomach was removed, washed with tap water, immersed in 3 mol/L brine, and the surface of the mucous membrane was wiped with a paper towel. The gastric mucous membrane was detached, chopped, and homogenized in a 0.25 mol/L saccharose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L saccharose solution, superimposed on a 0.25 mol/L saccharose solution containing 7.5% Ficoll, and centrifuged at 100,000×g for 5 hr. The fraction containing the interface between the both layers was recovered, and centrifugally washed with 0.25 mol/L saccharose solution. The obtained microsomal fraction was used as a proton, potassium-adenosine triphosphatase standard product.

To 40 μL of a 50 mmol/L HEPES-tris buffer (5 mmol/L magnesium chloride, 10 mmol/L potassium chloride, 10 μmol/L valinomycin, pH=6.5) containing 2.5 μg/mL (based on the protein concentration) of the enzyme standard product was added a test compound (5 μL) dissolved in a 10% aqueous dimethyl sulfoxide solution, and the mixture was incubated at 37° C. for 30 min. The enzyme reaction was started by adding 5 μL of a 2 mmol/L adenosine triphosphate tris salt solution (50 mmol/L HEPES-tris buffer (5 mmol/L magnesium chloride, pH 6.5)). The enzyme reaction was carried out at 37° C. for 20 min, and 15 μL of a malachite green solution (0.12% malachite green solution in sulfuric acid (2.5 mol/L), 7.5% ammonium molybdate and 11% Tween 20 were mixed at a ratio of 100:25:2) was added to quench the reaction. After allowing to stand at room temperature for 15 min, the resulting reaction product of inorganic phosphorus with malachite green was colorimetrically determined at a wavelength of 620 nm. In addition, the amount of the inorganic phosphoric acid in the reaction solution free of potassium chloride was measured in the same manner, which was subtracted from the inorganic phosphoric acid amount in the presence of potassium chloride to determine the proton, potassium-adenosine triphosphatase activity. The inhibitory rate (%) was determined from the activity value of the control and the activity values of various concentrations of the test compound, and the 50% inhibitory concentration ($IC_{50}$) of the proton, potassium-adenosine triphosphatase was determined. The results are shown in Table 4.

Experimental Example 2

The pKa values were calculated using Physchem Batch (Ver. 10) (Advanced Chemistry Development, Inc.). The results are shown in Table 4.

Experimental Example 3

ATP Content Test
Human liver cancer-derived cell line HepG2 (ATCC No. HB-8065) was passaged using Dulbecco's Modified Eagle medium (DMEM; Invitrogen) containing 10% fetal bovine serum (FBS; TRACE SCIENTIFIC LTD.), 1 mmol/L sodium pyruvate (Invitrogen), 2 mmol/L L-glutamine (Invitrogen), 50 IU/mL penicillin (Invitrogen) and 50 μg/mL streptomycin (Invitrogen) at 5% $CO_2$, 37° C. The test reagent was prepared with DMSO to 10 mM, and further diluted with DMEM medium containing 0.5% FBS, 1 mmol/L sodium pyruvate, 2 mmol/L L-glutamine, 50 IU/mL penicillin and 50 μg/mL streptomycin to a final concentration of DMSO of 0.1%. HepG2 ($2 \times 10^4$ cells/well) was cultured on a 96 well white plate (Costar) with the test reagent at 5% $CO_2$. 37° C. After culture for one day, the intracellular ATP content was measured using ATPLite™ (PerkinElmer Life Sciences). The results are shown in Table 4 (n≥3, average value±SD) as a relative value (%) to control (without addition of drug).

Experimental Example 4

Caspase-3/7 Activity Test
The Caspase-3/7 activity in the cells cultured for one day by a method similar to that in Experimental Example 3 was measured using CASPASE-GLO 3/7 Assay (Promega). The results are shown in Table 4 (n≥3, average value±SD) as relative activity (%) of each reagent based on the maximum value of Caspase-3/7 activity when exposed to Staurosporine (100%), and the activity without addition of a test reagent (0%).

Experimental Example 5

Figure 2:
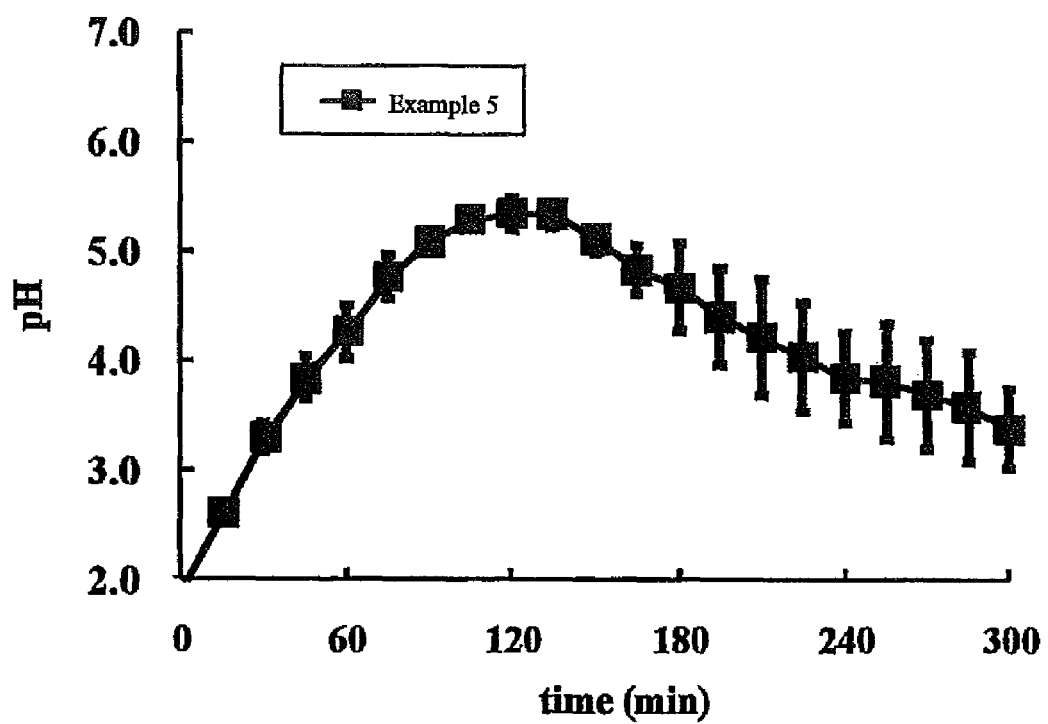
FIG. 2 shows results of perfusate pH measurement test in anesthetized rat stomach perfusion model in Example 5.
Figure 3:
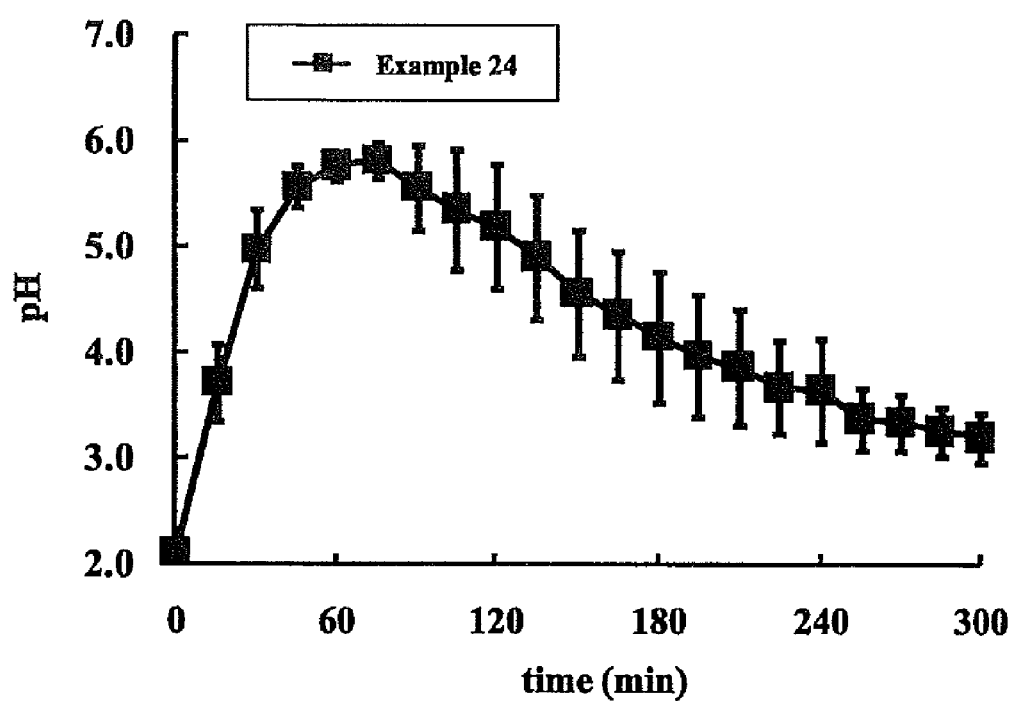
FIG. 3 shows results of perfusate pH measurement test in anesthetized rat stomach perfusion model in Example 24.

Measurement of Perfusate pH in Anesthetized Rat Stomach Reperfusion Model
Jcl:SD male rats (8-week-old) were fasted for about 24 hr and used for the experiment. The test compounds were dissolved in a DMAA:PEG400=1:1 solution to the dose of 1 mL/kg. Under anesthesia with urethane (1.2 g/kg, i.p.), cannulas were inserted from the duodenum and the forestomach into the stomach, the esophagus was ligated and the stomach was reperfused with physiological saline (0.5 mL/min). The perfusate was subjected to a continuous pH measurement using trace flow type glass electrodes (6961-15C and 2461A-15T, HORIBA). Histamine dihydrochloride (8 mg/kg/h) was continuously administered for 1 hr or longer by intravenous infusion. After the pH was stabilized, the test compound was intravenously administered. The pH of the perfusate was measured until 5 hours after administration of the test compound. The results are shown in FIGS. 1, 2 and 3.

TABLE 4

| Example No. | $H^+/K^+$-ATPase inhibitory activity ($IC_{50}$, nM) | pKa value (calculated) | ATP content (%, 100 μM) | Caspase-3/7 activity (%, 100 μM) |
|---|---|---|---|---|
| 2 | 100 | 7.84 | 85.5 | −1.1 |
| 3 | 100 | 7.77 | 86.5 | −0.5 |
| 4 | 140 | 7.79 | 84.5 | −0.6 |
| 5 | 200 | 7.73 | 88.9 | 0.3 |
| 8 | 180 | 7.81 | 76.7 | 2.4 |
| 10 | 280 | 7.79 | 80.0 | 0.9 |
| 23 | 83 | 7.84 | — | — |
| 24 | 140 | 7.84 | — | — |
| 25 | 200 | 7.73 | — | — |
| 26 | 130 | 7.73 | — | — |
| 27 | 160 | 7.73 | — | — |

From the results of Table 4, it is clear that compound (I) of the present invention has a superior $H^+/K^+$-ATPase inhibitory activity and a low pKa value, as well as extremely low cytotoxicity even when used at a high concentration. In addition, from the results of FIGS. 1, 2 and 3, it is clear that compound (I) has a moderate duration of action.

Industrial Applicability

Compound (I) of the present invention shows a superior proton pump inhibitory effect. Conventional proton pump inhibitors such as omeprazole, lansoprazole and the like are converted to active forms in an acidic environment of gastric parietal cells and form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ competitive manner, and consequently suppresses acid secretion. Therefore, it is sometimes called a potassium-competitive acid blocker (P-CAB), or an acid pump antagonist (APA). Compound (I) rapidly exhibits the action and shows the maximum efficacy from the initial administration. Furthermore, its metabolism is less influenced by metabolic polymorphism, and variation of efficacy among patients is small. In addition, it has been found that compound (I) is designed to have a characteristic chemical structure wherein (i) the substituent at the 5-position of pyrrole ring is a 2-F-3-pyridyl group, (ii) the substituent at the 4-position of pyrrole ring is a fluorine atom, and (iii) the 1-position of pyrrole ring is a 2-pyridylsulfonyl group or 3-pyridylsulfonyl group having at least one substituent, and such chemical structure is conducive to a strong proton pump inhibiting activity, and significantly decreases cytotoxicity. Furthermore, it is characterized in that substitution of the 4-position of pyrrole ring by a fluorine atom in compound (I) lowers basicity (pKa value) of methylaminomethyl moiety due to an electron withdrawing effect of the fluorine atom, and decreases the risk of toxicity expression derived from strong basicity, and that introduction of at least one substituent into A of compound (I) controls the duration of action optimally. Hence, the present invention can provide a clinically useful agent for the prophylaxis or treatment of peptic ulcer (e.g., gastric ulcer, duodenal ulcer, anastomotic ulcer, ulcer caused by non-steroidal anti-inflammatory drug, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia, gastric cancer, stomach MALT lymphoma or hyperacidity; or a suppressant of upper gastrointestinal bleeding due to peptic ulcer, acute stress ulcer, hemorrhagic gastritis or invasive stress; and the like. Since compound (I) shows low toxicity and is superior in water-solubility, in vivo kinetics and efficacy exhibition, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, onset of suppression of gastric acid secretion is rapid, and symptoms such as pain and the like can be alleviated rapidly.

While some of the embodiments of the present invention have been described in detail in the above, it will, however, be evident for those of ordinary skill in the art that various modifications and changes may be made to the particular embodiments shown without substantially departing from the novel teaching and advantages of the present invention. Such modifications and changes are encompassed in the spirit and scope of the present invention as set forth in the appended claims.

This application is based on patent application Nos. 2008-218851 and 2008-269099 filed in Japan, the contents of which are incorporated in full herein by this reference.

The invention claimed is:

1. A pharmaceutical composition comprising 1-{4-fluoro-5-(2-fluoropyridin-3-yl)-1-[(4-methylpyridin-2-yl)sulfonyl]-1H-pyrrol-3-yl}-N-methylmethanamine or a salt thereof and a pharmacologically acceptable carrier.

2. A method for inhibiting acid secretion in a mammal, which comprises administering an effective amount of 1-{4-fluoro-5-(2-fluoropyridin-3-yl)-1-[(4-methylpyridin-2-yl)sulfonyl]-1H-pyrrol-3-yl}-N-methylmethanamine or a salt thereof to a mammal.

3. A method for blocking potassium-competitive acid in a mammal, which comprises administering an effective amount of 1-{4-fluoro-5-(2-fluoropyridin-3-yl)-1-[(4-methylpyridin-2-yl)sulfonyl]-1H-pyrrol-3-yl}-N-methylmethanamine or a salt thereof to a mammal.

* * * * *